United States Patent
Si et al.

(10) Patent No.: US 11,952,530 B2
(45) Date of Patent: Apr. 9, 2024

(54) ARYL-SUBSTITUTED SACCHARIDES OR GLYCOSIDES AND USE THEREOF IN A DRILLING FLUID COMPOSITION

(71) Applicants: CHINA PETROLEUM & CHEMICAL CORPORATION, Beijing (CN); Sinopec Petroleum Engineering Technology Service Co., Ltd., Beijing (CN); Drilling Engineering Technology Research Inst. of Sinopec Zhongyuan Petroleum Engineering Co., LTD, Henan (CN); SINOPEC ZHONGYUAN PETROLEUM ENGINEERING CO., LTD, Henan (CN)

(72) Inventors: Xiqiang Si, Henan (CN); Zhonghua Wang, Henan (CN); Weiting Li, Henan (CN); Jun Wei, Henan (CN); Zhongjin Wang, Henan (CN); Yuebin Lv, Henan (CN)

(73) Assignees: CHINA PETROLEUM & CHEMICAL CORPORATION, Beijing (CN); Sinopec Petroleum Engineering Technology Service Co., Ltd., Beijing (CN); Drilling Engineering Technology Research Institute of Sinopec Zhongyuan Petroleum Engineering Co., LTD, Henan (CN); SINOPEC ZHONGYUAN PETROLEUM ENGINEERING CO., LTD, Henan (CN)

( * ) Notice: Subject to any disclaimer, the term of this patent is extended or adjusted under 35 U.S.C. 154(b) by 496 days.

(21) Appl. No.: 16/966,870

(22) PCT Filed: Nov. 29, 2019

(86) PCT No.: PCT/CN2019/121908
§ 371 (c)(1),
(2) Date: Jul. 31, 2020

(87) PCT Pub. No.: WO2020/119478
PCT Pub. Date: Jun. 18, 2020

(65) Prior Publication Data
US 2021/0040373 A1 Feb. 11, 2021

(30) Foreign Application Priority Data
Dec. 13, 2018 (CN) .......................... 201811525211.1

(51) Int. Cl.
*C09K 8/08* (2006.01)
*C07H 15/207* (2006.01)

(52) U.S. Cl.
CPC ............ *C09K 8/08* (2013.01); *C07H 15/207* (2013.01)

(58) Field of Classification Search
None
See application file for complete search history.

(56) References Cited

U.S. PATENT DOCUMENTS

| | | | |
|---|---|---|---|
| 2,360,327 A * | 10/1944 | Horace | C09K 8/206 47/DIG. 10 |
| 2006/0105919 A1* | 5/2006 | Colaco | C09K 8/584 507/209 |

(Continued)

FOREIGN PATENT DOCUMENTS

| CN | 104140525 A | 11/2014 |
|---|---|---|
| CN | 104497188 A | 4/2015 |

(Continued)

*Primary Examiner* — John J Figueroa
(74) *Attorney, Agent, or Firm* — NKL Law; Allen Xue

(57) ABSTRACT

An aryl-substituted saccharide or glycoside or a mixture of a plurality of aryl-substituted saccharides or glycosides have at least good resistance to high temperatures and salt, and lower filtration loss. These aryl-substituted saccharide or glycoside are used in making a drilling fluid composition. The aryl-substituted saccharide or glycoside or the mixture of a plurality of aryl-substituted saccharides or glycosides each or in combination bears a substituent A and a substituent B, wherein the substituent A contains a unit —O—R$_6$— in its structure and the substituent B contains a unit

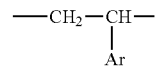

in its structure, and the substituents and the numbers are defined in the description.

19 Claims, 7 Drawing Sheets

(56) References Cited

U.S. PATENT DOCUMENTS

| | | | | |
|---|---|---|---|---|
| 2011/0214864 A1* | 9/2011 | Maghrabi | ................ | C09K 8/36 |
| | | | | 166/381 |
| 2012/0157353 A1* | 6/2012 | Breeden | ................... | C09K 8/24 |
| | | | | 507/119 |
| 2013/0303411 A1* | 11/2013 | Wagle | .................... | C09K 8/035 |
| | | | | 507/129 |

FOREIGN PATENT DOCUMENTS

| | | |
|---|---|---|
| CN | 106432375 A | 2/2017 |
| CN | 106432378 A | 2/2017 |
| CN | 106701046 A | 5/2017 |
| CN | 107973827 A | 5/2018 |
| CN | 107973880 A | 5/2018 |
| CN | 107987808 A | 5/2018 |
| WO | 9202594 A1 | 2/1992 |

\* cited by examiner

ARYL-SUBSTITUTED SACCHARIDES OR GLYCOSIDES AND USE THEREOF IN A DRILLING FLUID COMPOSITION

TECHNICAL FIELD

The present invention relates to aryl-substituted saccharides or glycosides, and more particularly to an aryl-substituted saccharide or glycoside or a mixture of a plurality of aryl-substituted saccharides or glycosides. The invention also relates to a drilling fluid composition produced from the aryl-substituted saccharides or glycosides and a process of producing the drilling fluid composition.

BACKGROUND

In recent years, with the increasing situations encountered in drilling deep wells, ultra-deep wells, highly deviated wells, horizontal wells and complex strata in the process of oil and gas exploration, the requirements on the filtration loss reduction of drilling fluid are more and more strict, and the filtration loss control of the drilling fluid is more difficult. If the control of the filtration loss of the drilling fluid is not good, a large amount of drilling fluid can invade into the stratum, the original stress balance of the stratum is damaged, and stress collapse and instability of the stratum may occur. Therefore, the control of the drilling fluid filtration loss has great significance for avoiding stratum stress collapse.

SUMMARY OF THE INVENTION

The inventors of the present invention have found that the drilling fluid of the prior art needs to be improved at least in terms of high temperature resistance, salt resistance, fluid loss reducing property and the like. For this reason, the present inventors have deeply studied and found aryl substituted saccharides or glycosides, and have completed the present invention based on the findings.

Specifically, the present invention relates to the following aspects.

1. An aryl-substituted saccharide or glycoside or a mixture of a plurality of aryl-substituted saccharides or glycosides, each or in combination, bearing a substituent a and a substituent B, wherein the substituent A contains in its structure a unit —O—R$_6$— (preferably —O—CH$_2$CH$_2$—, 

or any combination thereof), wherein R$_6$ is a C2-8 linear or branched alkylene or C2-6 linear or branched alkylene, Rc is a C1-5 linear or branched alkyl or C1-3 linear or branched alkyl, the substituent B contains in its structure a unit

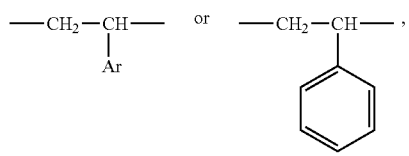

wherein Ar is an optionally substituted C6-20 aryl (preferably optionally substituted phenyl).

2. The aryl-substituted saccharide or glycoside or a mixture of a plurality of aryl-substituted saccharides or glycosides according to any one of the preceding or subsequent aspects, wherein the substituent A further contains in its structure a unit

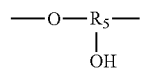

(preferably

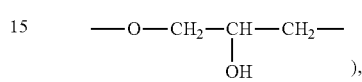), wherein R$_5$ is a C$_{3-6}$ linear or branched trivalent alkyl group (preferably trivalent propyl or trivalent butyl), and/or the substituent B further contains in its structure at least one group selected from group

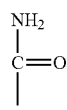

(preferably a unit

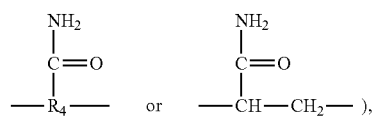), group-SO$_3$M (preferably unit

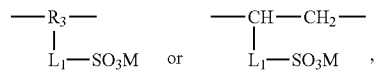

especially

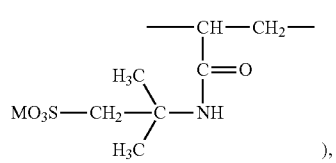), unit

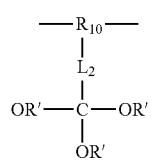

(preferably

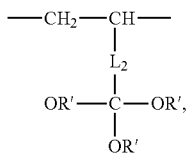

especially

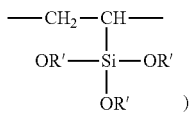

)

and group —COOM (preferably unit

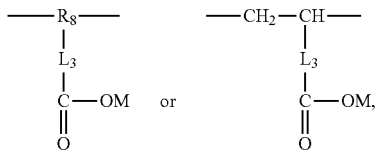

especially

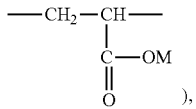

), $R_4$ is a C2-6 linear or branched alkylenyl group (preferably ethylene or propylene group), R3 is C2-6 linear or branched alkylene (preferably ethylene or propylene group), $L_1$ is any linking group preferably having no more than 10 carbon atoms (preferably a single bond, C2-10 linear or branched alkylene, —C(=O)—C2-10 linear or branched alkylene, —C(=O)O—C2-10 linear or branched alkylene, —C(=O)NH—C2-10 linear or branched alkylene, C2-5 linear or branched alkylene-C(=O)—C2-5 linear or branched alkylene, C2-5 linear or branched alkylene-C(=O)O—C2-5 linear or branched alkylene, C2-5 linear or branched alkylene-C(=O)NH—C2-5 linear or branched alkylene, more preferably —C(=O)NH—C2-10 linear or branched alkylene), M is hydrogen, an alkali metal (such as K or Na), or ammonium ($NH_4$), $R_{10}$ is C2-6 linear or branched alkylene (preferably ethylene or propylene group), $L_2$ is any linking group preferably having no more than 10 carbon atoms (preferably single bond or C2-10 linear or branched alkylene, especially single bond), $L_3$ is any linking group preferably having no more than 10 carbon atoms (preferably a single bond or C2-10 linear or branched alkylene, especially a single bond), R' is a C1-4 linear or branched alkyl (preferably methyl or ethyl), $R_8$ is a C2-6 linear or branched alkylene (preferably ethylene or propylene group).

3. The aryl-substituted saccharide or glycoside or a mixture of a plurality of aryl-substituted saccharides or glycosides according to any one of the preceding or subsequent aspects, wherein the substituent A is represented schematically by the following formula (A-1), formula (A-2) or formula (A-3),

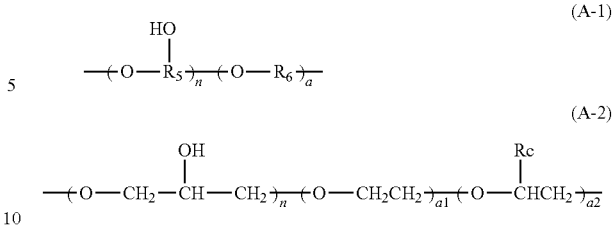

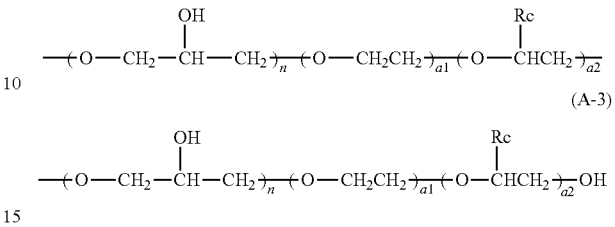

in these formulae, n is a number ranging from 0 to 10 (e.g., 0), a is a number ranging from 1 to 20 (e.g., 5 to 15 or 8 to 12), a1 is a number ranging from 0 to 20 (e.g., a number ranging from 0 to 10 or from 0 to 5), a2 is a number ranging from 1 to 20 (e.g., a number ranging from 5 to 15 or from 8 to 12), the substituent B is represented schematically by the following formula (B-1), formula (B-2) or formula (B-3),

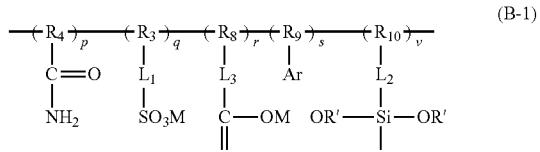

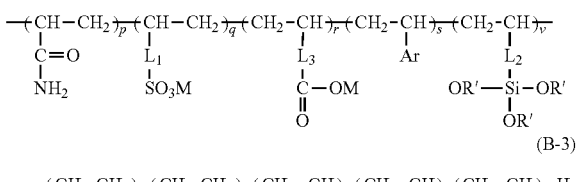

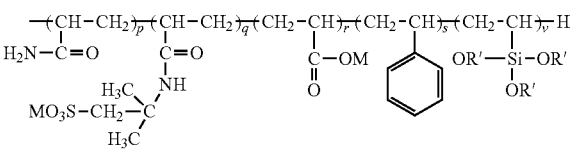

in these formulae, $R_9$ is ethylene, p is a number ranging from 0 to 30 or from 2 to 30 (preferably a number ranging from 5 to 25 or from 10 to 20), q is a number ranging from 0 to 30 or from 2 to 30 (preferably a number ranging from 5 to 25 or from 10 to 20), r is a number ranging from 0 to 30 or from 2 to 30 (preferably a number ranging from 5 to 25 or from 10 to 20), s is a number ranging from 2 to 30 (preferably a number ranging from 5 to 25 or from 10 to 20), and v is a number ranging from 0 to 30 (preferably a number ranging from 1 to 20 or from 4 to 12).

4. The aryl-substituted saccharide or glycoside or a mixture of a plurality of aryl-substituted saccharides or glycosides according to any one of the preceding or subsequent aspects, wherein the saccharide or glycoside is a glucose residue or glucose glycoside residue represented schematically by the following formula (1), (1)

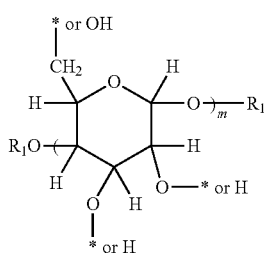

in formula (1), two occurrences of $R_1$, same as or different from one another, are each independently selected from the group consisting of hydrogen and C1-20 linear or branched alkyl group (preferably each independently selected from the group consisting of hydrogen and C5-20 linear or branched alkyl group, more preferably each independently selected from the group consisting of hydrogen and C8-18 linear or branched alkyl group, more preferably octyl, decyl, dodecyl, tetradecyl, hexadecyl or octadecyl), m is an integer of 1-3 or 2, and * represents the bonding point of the substituent A or the substituent B, provided that there are at least two of the bonding points.

5. The aryl-substituted saccharide or glycoside or a mixture of a plurality of aryl-substituted saccharides or glycosides according to any one of the preceding or subsequent aspects, being one or more compounds selected from compounds represented schematically by the following formula (I-1), formula (I-2), formula (I-3) or formula (I-4), (I-1)

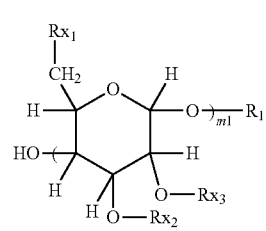

in formula (I-1), among m1 number of $Rx_1$, one $Rx_1$ is said substituent A, while the remaining $Rx_1$, same as or different from each other, are each independently selected from said substituent A and hydroxyl group, wherein m1 is an integer of 2 to 3, and m1 number of $Rx_2$ and m1 number of $Rx_3$, same as or different from each other, are each independently selected from the group consisting of hydrogen atom and said substituent B, provided that at least one of these $Rx_2$ and $Rx_3$ is said substituent B, (I-2)

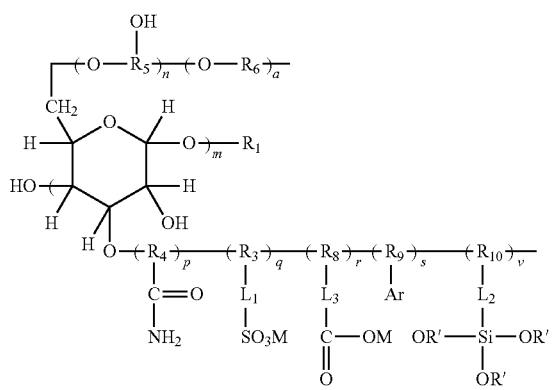

(I-3)

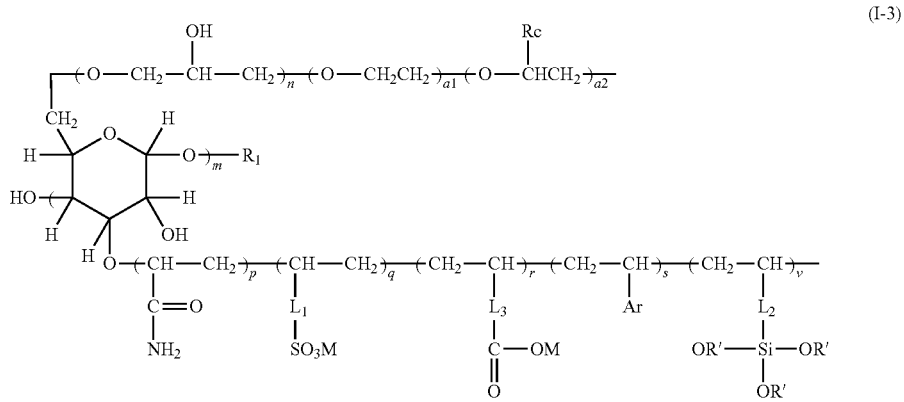

-continued

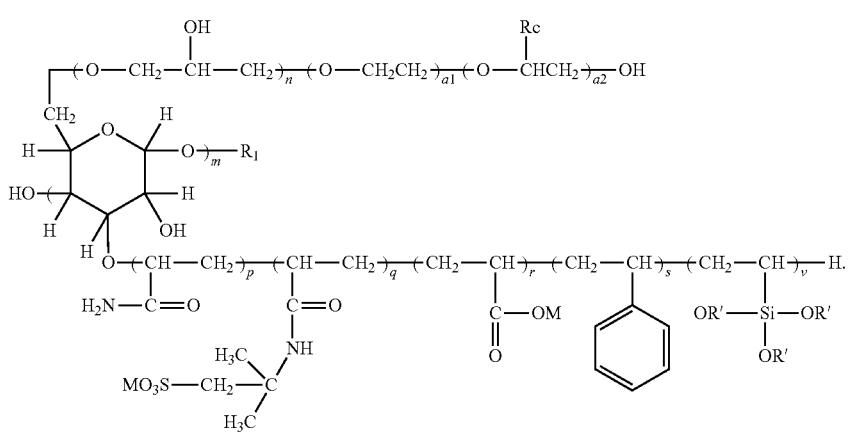
(I-4)

6. The aryl-substituted saccharide or glycoside or a mixture a mixture of a plurality of aryl-substituted saccharides or glycosides according to any one of the preceding or subsequent aspects, having an amine value of from 0.10 to 0.80 mmol/g, preferably from 0.20 to 0.50 mmol/g.

7. A process of producing an aryl-substituted saccharide or glycoside or a mixture of a plurality of aryl-substituted saccharides or glycosides, comprising the steps of:
  1) reacting a saccharide or glycoside represented schematically by the following formula (X-1) or formula (X-2) (preferably at least one selected from octyl glycoside, decyl glycoside, dodecyl glycoside, tetradecyl glycoside, hexadecyl glycoside or octadecyl glycoside), with an etherifying agent (preferably an alkylene oxide monomer represented schematically by the following formula (A-11), a polyhydroxyl monomer represented schematically by the following formula (A-21) or a combination thereof, particularly preferably at least one selected from the group consisting of propylene oxide, 1,2-butylene oxide and 1,2-pentylene oxide), optionally in the presence of a catalyst (preferably an alkaline catalyst, particularly preferably at least one selected from the group consisting of sodium carbonate, potassium carbonate, calcium oxide and magnesium oxide), to obtain an etherified saccharide or glycoside,

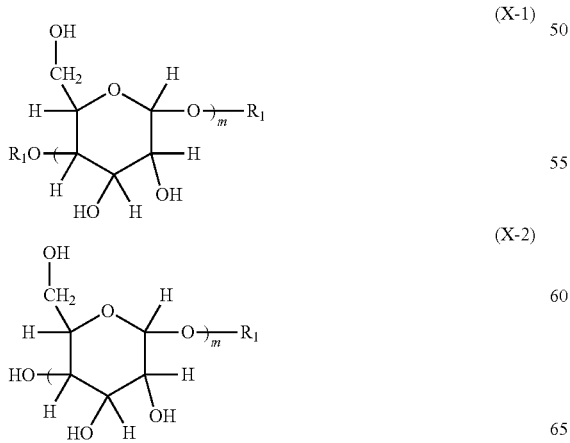

in formula (X-1) and formula (X-2), two occurrences of $R_1$, same as or different from one another, are each independently selected from the group consisting of hydrogen and C1-20 linear or branched alkyl group (preferably each independently selected from the group consisting of hydrogen and C5-20 linear or branched alkyl group, more preferably each independently selected from the group consisting of hydrogen and C8-18 linear or branched alkyl group, more preferably octyl, decyl, dodecyl, tetradecyl, hexadecyl or octadecyl), and m is an integer of 1-3 or 2,

(A-11)

in formula (A-11), Ra is a hydrogen atom or C1-5 linear or branched alkyl group, preferably a hydrogen atom or $C_{1-3}$ linear or branched alkyl group,

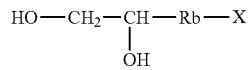
(A-21)

in formula (A-21), Rb is a C1-4 linear or branched alkylenyl group or a C1-2 linear or branched alkylenyl group, and X is a hydroxyl group or a halogen atom (such as Cl or Br), 2) reacting the etherified saccharide or glycoside with an arylethylene monomer represented schematically by the following formula (B-11) or formula (B-12), optionally using an acrylamide monomer represented schematically by the following formula (B-21), optionally using a sulfoethylene monomer represented schematically by the following formula (B-31) or formula (B-32), optionally using a siloxyethylene monomer represented schematically by the following formula (B-41) or formula (B-42), and optionally using a carboxyethylene monomer represented schematically by the following formula (B-51) or formula (B-52) for the reaction (preferably, by a radical polymerization in the presence of an initiator, preferably at least one initiator selected from the group consisting of ammonium persulfate, potassium persulfate, ceric ammonium nitrate, azobisisobutyronitrile, dimethyl azobisisobutyrate and azobisisobutylamidine hydrochloride), to obtain the aryl-substituted saccharide or glycoside or the mixture of a plurality of aryl-substituted saccharides or glycosides,

  (B-11)

in formula (B-11), Ar is an optionally substituted $C_{6-20}$ aryl group (preferably an optionally substituted phenyl group),

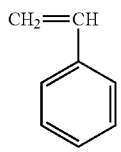  (B-12)

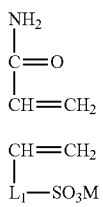  (B-21)

(B-31)

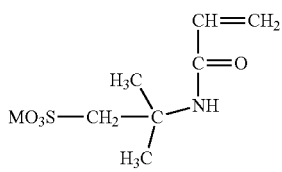  (B-32)

in formula (B-31) and formula (B-32), $L_1$ is any linking group preferably having no more than 10 carbon atoms (preferably a single bond, C2-10 linear or branched alkylene, —C(=O)—C2-10 linear or branched alkylene, —C(=O)O—C2-10 linear or branched alkylene, —C(=O)NH—C2-10 linear or branched alkylene, C2-5 linear or branched alkylene-C(=O)—C2-5 linear or branched alkylene, C2-5 linear or branched alkylene-C(=O)O—C2-5 linear or branched alkylene, C2-5 linear or branched alkylene-C(=O)NH—C2-5 linear or branched alkylene), more preferably-C(=O)NH—C2-10 linear or branched alkylene), and M is hydrogen, alkali metal (such as K or Na) or ammonium ($NH_4$),

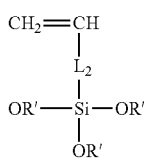  (B-41)

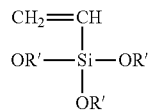  (B-42)

in formula (B-41) and formula (B-42), $L_2$ is any linking group preferably having no more than 10 carbon atoms (preferably a single bond or C2-10 linear or branched alkylenyl group, particularly a single bond), and R' is C1-4 linear or branched alkyl group (preferably methyl or ethyl),

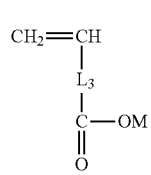  (B-51)

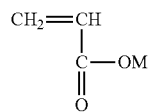  (B-52)

in formula (B-51) and formula (B-52), $L_3$ is any linking group preferably having no more than 10 carbon atoms (preferably a single bond or C2-10 linear or branched alkylenyl group, particularly a single bond), and M is hydrogen, alkali metal (such as K or Na), or ammonium ($NH_4$).

8. The production process according to any one of the preceding or subsequent aspects, wherein the reaction in step 1) is conducted at a temperature of 95 to 155° C. for 1 to 3 hours, and/or the reaction in step 2) is conducted at a temperature of 40 to 80° C. for 1 to 3 hours, and/or the weight ratio of the etherifying agent, the saccharide or glycoside and the catalyst is 24:(70-100):(10-30), preferably 24:(75-95):(15-25), most preferably 24:(80-90): 20, and/or the weight ratio of the etherifying agent, the carboxyethylene monomer (such as acrylic acid), the arylethylene monomer (such as styrene), the acrylamide monomer (such as acrylamide), the sulfoethylene monomer (such as 2-acrylamido-2-methylpropanesulfonic acid), the siloxyethylene monomer (such as vinyltriethoxysilane), and the initiator is 24:(20-40):(20-40):(20-40):(10-20):(10-20):(0.6-1.8), preferably 24:(25-35):(25-35):(25-35):(12-18):(12-18):(0.8-1.6), most preferably 24:30:30:30:(14-16):(14-16):(1.0-1.4).

9. A drilling fluid composition, comprising an aryl-substituted saccharide or glycoside and a base slurry, wherein the aryl-substituted saccharide or glycoside is an aryl-substituted saccharide or glycoside or a mixture of a plurality of aryl-substituted saccharides or glycosides according to any one of the preceding or subsequent aspects, or an aryl-substituted saccharide or glycoside or a mixture of a plurality of aryl-substituted saccharides or glycosides produced by the production process according to any one of the preceding or subsequent aspects.

10. The drilling fluid composition according to any one of the preceding or subsequent aspects, wherein the aryl-substituted saccharide or glycoside is present in an amount of 0.1 to 5 wt % (preferably 0.5 to 1.5 wt % or 0.8 to 1.2 wt %) based on 100 wt % of the total weight of the drilling fluid composition.

11. A process of producing a drilling fluid composition, comprising the step of mixing an aryl-substituted saccharide or glycoside with a base slurry, wherein the aryl-substituted saccharide or glycoside is one aryl-substituted saccharide or glycoside or a mixture of a plurality of aryl-substituted saccharides or glycosides according to any one of the preceding or following aspects or is produced by the process of producing according to any one of the preceding or following aspects.

Technical Effects

According to the aryl-substituted saccharide or glycoside or the drilling fluid composition produced therefrom of the present invention, at least one of the following technical effects may be achieved:
  (1) ability of being compounded with water-based drilling fluid in any proportion, without influence to the performance of the drilling fluid;
  (2) no biotoxicity, being green and environmentally friendly;
  (3) good high-temperature resistance, salt resistance and filtrate loss reduction;
  (4) good inhibition performance, lubricity and compatibility; and
  (5) applicability for stratums with high temperature, salt-gypsum stratums and fracture bedding development stratums, and ability of reducing the amount of the drilling fluid invading the stratums, reducing the influence of the drilling fluid on the stratums, and avoiding collapse and block falling caused by stratum stress change, so as to achieve green, safe and efficient drilling.

DRAWINGS

EMBODIMENTS OF THE INVENTION

Figure 1:
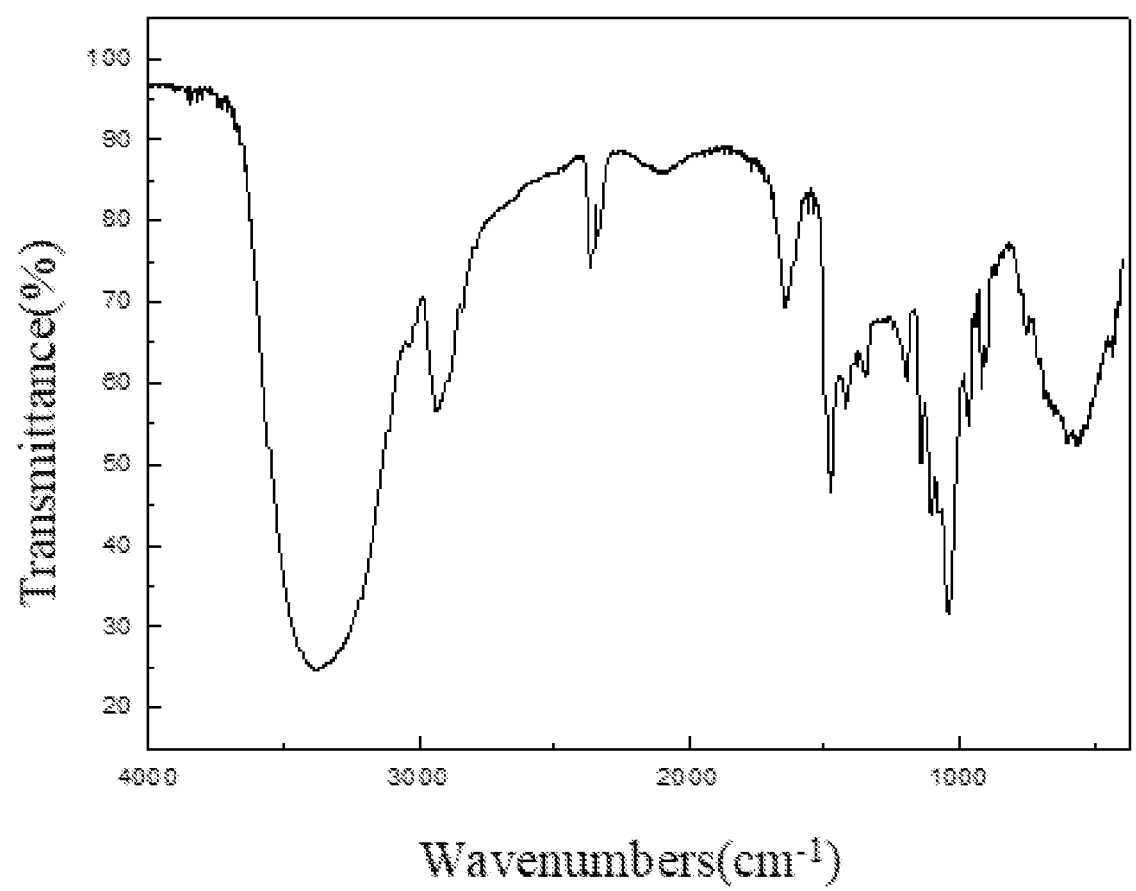
FIG. 1 is an infrared spectrum of an aryl-substituted saccharide or glycoside obtained in Example 1 of the present invention.

The embodiments of the present invention will be illustrated in more detail below, but it should be understood that the scope of the invention is not limited by the embodiments, but is defined by the claims appended.

All publications, patent applications, patents, and other references mentioned in this specification are herein incorporated by reference in their entirety. Unless defined otherwise, all technical and scientific terms used herein are understood same as the meanings commonly known to those skilled in the art. In case of conflict, definitions according to the present specification will control.

When the specification introduces materials, substances, processes, steps, devices, components, or the like initiated with "known to those ordinary skill in the art", "prior art", or the like, it is intended that the subject matter so initiated encompass not only those conventionally used in the art at the time of filing this application, but also those may not be so commonly used at the present time, but will become known in the art as being suitable for a similar purpose.

In the context of the present specification, the numerical values include integers and fractions.

In the context of the present specification, $R_9$ is an ethylene group.

In the context of the present description, the measurement of amine value comprises: 0.5 g of the sample to be tested (with accuracy to 0.0001 g) is weighed into a clean and dry 250 mL conical flask, 50 mL of deionized water is added and the total weight $m_1$ is recorded. 5 drops of bromocresol green-methyl red indicator are added into the solution to be detected, shaken uniformly, and titration is made at a constant speed using a standard solution of hydrochloric acid dropwise. The color change of the solution is observed carefully while shaking uniformly. When the color of the solution is changed from green to dark red, it is determined to be the titration end point. The volume V of the hydrochloric acid standard solution consumed is recorded. A blank test is carried out simultaneously. Amine value measurement is made for randomly sampled 3 batches of the test samples. The amine value is calculated according to formula (2):

$$\text{Amine value} = \frac{C_{HCl} \times (V - V_{blank})}{m} \quad (2)$$

in the formula:
Total amine value—calculated as $H^+$, in the unit of millimoles per gram (mmol/g);
$C_{HCl}$—concentration of hydrochloric acid standard solution used, in moles per liter (mol/L);
V—value of the volume of the hydrochloric acid-isopropanol standard solution consumed by the sample to be detected, in milliliter (mL);
Blank—value of the blank hydrochloric acid solution, in milliliters (mL);
m—accurate value of the weight of the sample to be measured, in gram (g).

In the context of the present specification, the expression "optionally substituted" means being optionally substituted (at a feasible position) by one or more (such as 1 to 5, 1 to 4, 1 to 3, 1 to 2 or 1) groups selected from the group consisting of halogen, hydroxy, mercapto, amino, aminocarbonyl, nitro, oxo, thio, cyano, $C_{1-6}$ linear or branched (halo) alk (oxy, thio, amino, carbonyl)yl, $C_{2-6}$ linear or branched (halo) alken (oxy, thio, amino, carbonyl)yl, $C_{2-6}$ linear or branched (halo) yne (oxy, thio, amino, carbonyl)yl, $C_{3-20}$ cycloalkyl, $C_{3-20}$ cycloalk (oxy, thio, amino)yl, $C_{3-20}$ cycloalkyl $C_{1-6}$ linear or branched (halo) alk (oxy, thio, amino, carbonyl)yl, $C_{3-20}$ cycloalkyl $C_{2-6}$ linear or branched (halo) alken (oxy, thio, amino, carbonyl)yl, $C_{3-20}$ cycloalkyl $C_{2-6}$ linear or branched (halo) alkyn (oxy, thio, amino, carbonyl)yl, $C_{3-20}$ cycloalkenyl, $C_{3-20}$ cycloalken (oxy, thio, amino)yl, $C_{3-20}$ cycloalkenyl $C_{1-6}$ linear or branched (halo) alk (oxy, thio, amino, carbonyl)yl, $C_{3-20}$ cycloalkenyl $C_{2-6}$ linear or branched (halo) alken (oxy, thio, amino, carbonyl)yl, $C_{3-20}$ cycloalkenyl $C_{2-6}$ linear or branched (halo) alkyn (oxy, thio, amino, carbonyl)yl, $C_{6-20}$ aryl, $C_{6-20}$ aryl (oxy, thio, amino) group, $C_{6-20}$ aryl $C_{1-6}$ linear or branched (halo)

alk (oxy, thio, amino, carbonyl)yl, $C_{6-20}$ aryl $C_{2-6}$ linear or branched (halo) alken (oxy, thio, amino, carbonyl)yl, $C_{6-20}$ aryl $C_{2-6}$ linear or branched (halo) alkyn (oxy, sulfur, amino, carbonyl)yl, $C_{4-20}$ heteroaryl group, $C_{4-20}$ heteroaryl (oxygen, sulfur, ammonia) group, $C_{4-20}$ heteroaryl $C_{1-6}$ linear or branched (halo) alk (oxygen, sulfur, ammonia, carbonyl)yl, $C_{4-20}$ heteroaryl $C_{2-6}$ linear or branched (halo) alken (oxygen, sulfur, ammonia, carbonyl)yl, $C_{4-20}$ heteroaryl $C_{2-6}$ linear or branched (halo) alkyn (oxygen, sulfur, ammonia, carbonyl)yl, $C_{2-20}$ heterocyclyl, $C_{2-20}$ heterocyclyl (oxygen, sulfur, ammonia) group, $C_{2-20}$ heterocyclyl $C_{1-6}$ linear or branched (halo) alk (oxygen, sulfur, ammonia, carbonyl)yl, $C_{2-20}$ heterocyclyl $C_{2-6}$ linear or branched (halo) alken (oxygen, sulfur, ammonia, carbonyl)yl, and $C_{2-20}$ heterocyclyl $C_{2-6}$ linear or branched (halo) alkyn (oxygen, sulfur, ammonia, carbonyl)yl. When more than one of these substituents are present, adjacent two substituents (for example, molecular chain ends of two substituents) may be bonded to one another to form a divalent substituent structure. For example, two adjacent $C_{1-6}$ linear or branched alkyl groups may be bonded to one another to form a corresponding alkylenyl group structure. Alternatively, two adjacent $C_{1-6}$ linear or branched alkoxy groups may for example form a corresponding alkylenedioxy structure, two adjacent $C_{1-6}$ linear or branched alkylamino groups may for example form a corresponding alkylenediamino structure, and two adjacent $C_{1-5}$ linear or branched alkylthio groups may for example form a corresponding alkylenedithio structure, etc. Examples of preferable substituents include halogen, $C_{1-6}$ linear or branched alkyl, and the like. Here, the expression "(halo) alk (oxy, thio, amino, carbonyl)yl" means: alkyl, haloalkyl, alkoxy, alkylthio, alkylamino, alkylcarbonyl, haloalkoxy, haloalkylthio, haloalkylamino or haloalkylcarbonyl; the expression "(halo) alken (oxy, thio, amino, carbonyl)yl" means: alkenyl, haloalkenyl, alkenyloxy, alkenylthio, alkenylamino, alkenylcarbonyl, haloalkenyloxy, haloalkenylthio, haloalkenylamino or haloalkenylcarbonyl; the expression "(halo) alkyn (oxy, thio, amino, carbonyl)yl" means: alkynyl, haloalkynyl, alkynyloxy, alkynylthio, alkynylamino, alkynylcarbonyl, haloalkynyloxy, haloalkynylthio, haloalkynylamino or haloalkynylcarbonyl; and the expression "(oxy, thio, amino) group" means oxy, thio or amino group. Here, the halo includes mono-, di-, tri-, or per-halo, etc.

All percentages, parts, ratios, etc. involved in this description are provided by weight, while pressures are gauge pressures, unless explicitly indicated.

In the context of this description, any two or more embodiments of the invention may be combined in any manner, and the resulting solution is a part of the original disclosure of this description, and is within the scope of the invention.

According to an embodiment of the present invention, it relates to one/a aryl-substituted saccharide or glycoside or a mixture of a plurality of aryl-substituted saccharides or glycosides. The term "one/a aryl-substituted saccharide or glycoside" as used herein refers to a sole aryl-substituted saccharide or glycoside present as a single compound, and the term "a mixture of a plurality of aryl-substituted saccharides or glycosides" refers to a mixture of two or more (i.e., a plurality of) aryl-substituted saccharides or glycosides. For the present invention, whether the aryl-substituted saccharide or glycoside of the present invention is present in the form of respective compound independently or in the form of a mixture with each other, the intended purpose of the present invention can be achieved without any particular limitation. Thus, the present invention sometimes refers collectively to the one aryl-substituted saccharide or glycoside and the plurality of aryl-substituted saccharides or glycosides collectively as aryl-substituted saccharide or glycoside or substituted saccharide or glycoside.

According to an embodiment of the present invention, the aryl-substituted saccharide or glycoside bears, either individually or in combination, a substituent A and a substituent B. Here, the so-called "bear individually" or the like means that the substituent A and the substituent B are each located on different aryl-substituted saccharide or glycoside molecules, while the so-called "bear in combination" or the like means that the substituent A and the substituent B may be either located on different aryl-substituted saccharide or glycoside molecules, respectively, or located on different or the same aryl-substituted saccharide or glycoside molecules in any combination (for example, two-by-two combination or a combination of all the three).

According to an embodiment of the present invention, the substituent A contains in its structure a unit —O—$R_6$—, preferably

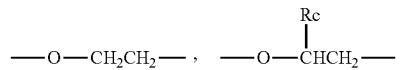

or any combination thereof. Here, $R_6$ is a $C_{2-8}$ linear or branched alkylenyl group or $C_{2-6}$ linear or branched alkylenyl group, and Rc is a $C_{1-5}$ linear or branched alkyl group or $C_{1-3}$ linear or branched alkyl group, more preferably a methyl group, ethyl group or propyl group. Here, the presence of the unit —O—$R_6$— or the substituent A may be determined by an infrared analysis method. For example, the presence of the unit

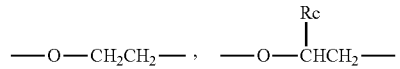

or substituent A, can be determined by an IR spectrum of the aryl-substituted saccharide or glycoside (including the aryl-substituted glycoside component described herein below) showing characteristic peaks at 1140-1175 $cm^{-1}$.

According to an embodiment of the invention, the substituent A also contains in its structure a unit

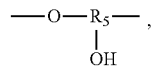

preferably

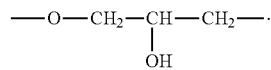

Here, $R_5$ is a C3-6 linear or branched trivalent alkyl group, preferably trivalent propyl or trivalent butyl.

According to an embodiment of the present invention, the substituent A is represented schematically by the following formula (A-1), formula (A-2) or formula (A-3). In the context of the present description, the expression "represent (ed) schematically" means, taking the formula (A-1) as an example, that the substituent A, although comprising "n" number of units

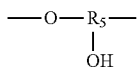

and "a" number of units —O—R$_6$— in one molecule as shown in formula (A-1), does not limit that the "n" number of units

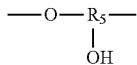

must be directly bonded to each other as shown in the formula to form a block structure, or that the "a" number of units —O—R$_6$— must be directly bonded to each other as shown in the formula to form a block structure, nor limit that the unit —O—R$_6$— and the unit

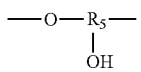

must be bonded in the specific order shown in the formula. Actually, according to the spirit of the present invention, the unit —O—R$_6$— and the unit

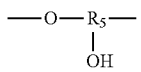

may be bonded in any order to form a random, block or alternating structure, and these structures are not particularly limited and fall within the intended scope of the present invention. Other formulas in the description can be similarly understood.

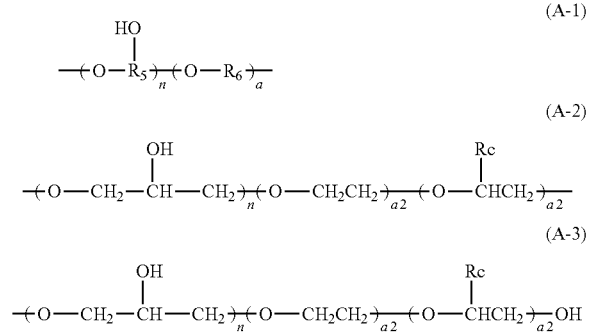

According to an embodiment of the invention, in these formulae, n is a number ranging from 0 to 10 (e.g. 0), a is a number ranging from 1 to 20 (e.g. 5 to 15 or 8 to 12), a1 is a number ranging from 0 to 20 (e.g. 0 to 10 or 0 to 5) and a2 is a number ranging from 1 to 20 (e.g. 5 to 15 or 8 to 12). In these formulae, all substituents and numbers which are not explicitly defined (e.g. R$_5$, R$_6$ etc.) apply directly to the corresponding definitions in substituent A.

According to an embodiment of the invention, the substituent B contains in its structure a unit

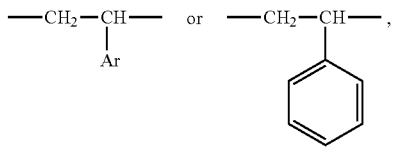

wherein Ar is an optionally substituted C$_{6-20}$ aryl, preferably optionally substituted phenyl. Here, the presence of the units

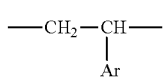

(in particular

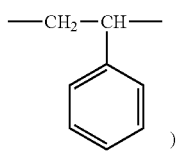

)

or the substituent B can be determined by infrared analysis. For example, the presence of the unit

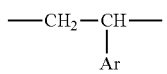

(particularly

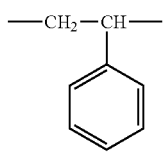

)

or the substituent B can be determined by an IR spectrum of the aryl-substituted saccharide or glycoside (including the aryl-substituted glycoside component described herein below) showing characteristic peaks at 1400-1600 cm$^{-1}$.

According to an embodiment of the invention, the substituent B also contains in its structure a group

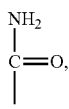

preferably a unit

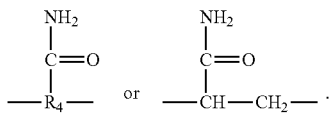

Here, R$_4$ is a C2-6 linear or branched alkylenyl group, preferably ethylene or propylene group. Here, the presence of the group

can be determined by an infrared analysis method. For example, the presence of the group

can be determined by an IR spectrum of the aryl-substituted saccharide or glycoside (including the aryl-substituted glycoside component described herein below) showing characteristic peaks at 1680-1699 cm$^{-1}$ and 1170-1290 cm$^{-1}$.

According to an embodiment of the invention, the substituent B also contains in its structure a group —SO$_3$M, preferably a unit

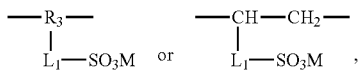

in particular

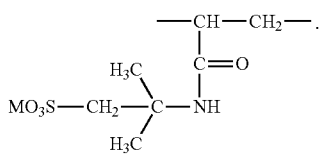

Here, R$_3$ is a C2-6 linear or branched alkylenyl group, preferably ethylene or propylene group. In addition, L$_1$ is any linking group, particularly any linking group having no more than 10 carbon atoms, preferably a single bond, C2-10 linear or branched alkylenyl, —C(=O)—C2-10 linear or branched alkylenyl, —C(=O)O—C2-10 linear or branched alkylenyl, —C(=O)NH—C2-10 linear or branched alkylenyl, C2-5 linear or branched alkylenyl-C(=O)—C2-5 linear or branched alkylenyl, C2-5 linear or branched alkylenyl-C(=O)O—C2-5 linear or branched alkylenyl, C2-5 linear or branched alkylenyl-C(=O)NH—C2-5 linear or branched alkylenyl, more preferably-C(=O)NH—C2-10 linear or branched alkylenyl. M is hydrogen, alkali metal (such as K or Na) or ammonium (NH$_4$). Here, the presence of the group —SO$_3$M can be determined by infrared analysis. For example, the presence of the group —SO$_3$M can be determined by an IR spectrum of the aryl-substituted saccharide or glycoside (including the aryl-substituted glycoside component described herein below) showing characteristic peaks at 1090-1180 cm$^{-1}$ and 940-990 cm$^{-1}$.

According to an embodiment of the invention, the substituent B also contains in its structure a unit

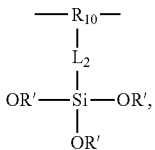

preferably

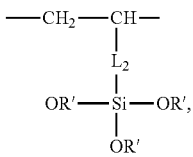

in particular

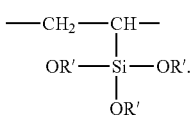

Here, R$_{10}$ is a C2-6 linear or branched alkylenyl group, preferably ethylene or propylene group. In addition, L$_2$ is any linking group, particularly any linking group having no more than 10 carbon atoms, preferably a single bond or C2-10 linear or branched alkylenyl group, particularly a single bond. R' is a C1-4 linear or branched alkyl group, preferably methyl or ethyl. Here, the presence of the unit

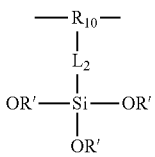

can be determined by an infrared analysis method. For example, the presence of the unit

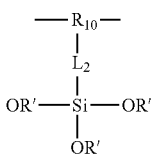

can be determined by an IR spectrum of the aryl-substituted saccharide or glycoside (including the aryl-substituted glycoside component described herein below) showing characteristic peaks at 1020-1060 cm$^{-1}$ and 1090-1120 cm$^{-1}$.

According to an embodiment of the invention, the substituent B also contains in its structure a group —COOM, preferably a unit

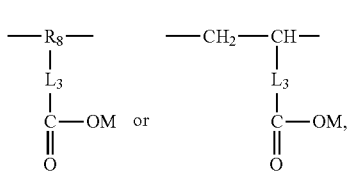

in particular

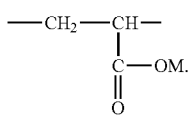

Here, $R_8$ is a C2-6 linear or branched alkylenyl group, preferably ethylene or propylene group. In addition, $L_3$ is any linking group, particularly any linking group having no more than 10 carbon atoms, preferably a single bond or C2-10 linear or branched alkylenyl group, particularly a single bond. M is hydrogen, an alkali metal (such as K or Na) or ammonium ($NH_4$). Here, the presence of the group —COOM can be determined by infrared analysis. For example, the presence of the group —COOM can be determined by an IR spectrum of the aryl-substituted saccharide or glycoside (including the aryl-substituted glycoside component described herein below) showing characteristic peaks at 1400-1420 $cm^{-1}$ and 3200-3400 $cm^{-1}$.

According to an embodiment of the present invention, the substituent B is represented schematically by the following formula (B-1), formula (B-2) or formula (B-3).

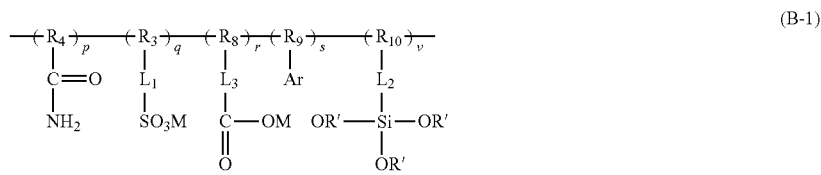

(B-1)

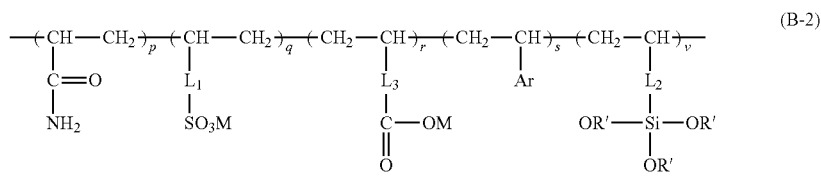

(B-2)

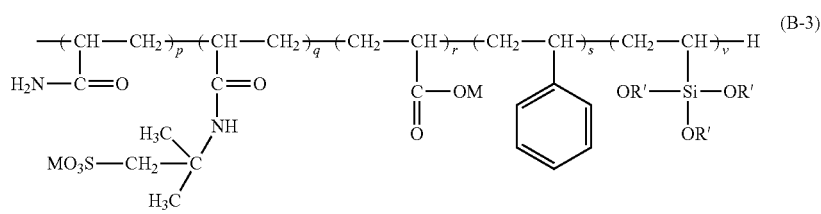

(B-3)

According to an embodiment of the invention, in these formulae, p is a number ranging from 0 to 30 or from 2 to 30 (preferably a number ranging from 5 to 25 or from 10 to 20, most preferably 15), q is a number ranging from 0 to 30 or from 2 to 30 (preferably a number ranging from 5 to 25 or from 10 to 20, most preferably 15), r is a number ranging from 0 to 30 or from 2 to 30 (preferably a number ranging from 5 to 25 or from 10 to 20, most preferably 15), s is a number ranging from 2 to 30 (preferably a number ranging from 5 to 25 or from 10 to 20, most preferably 15), and v is a number ranging from 0 to 30 (preferably a number ranging from 1 to 20 or from 4 to 12). In these formulae, all substituents and numbers which are not explicitly defined (e.g. $R_3$, $R_4$, M, etc.) apply directly to the corresponding definitions in substituent B.

According to an embodiment of the present invention, the saccharide or glycoside is a glucose residue or a glucoside residue represented schematically by the following formula (1).

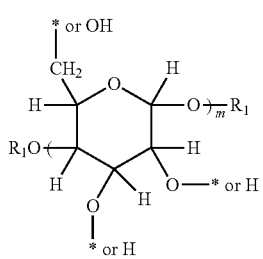

(1)

According to the present invention, the glucose residue or glucoside residue represented schematically by said formula (1) is a group obtained by removing the corresponding —OH or —H from a glucose or glucoside represented schematically by the following formula (1'). In the context of the present invention, said formula (1') may also be represented by formula (11') or formula (12'), but neither formula (1'), formula (11') nor formula (12') is intended to limit the steric configuration of any glucose or glucose glycoside according to the present invention or of any glucose residue or glucose glycoside residue according to the present invention. Here, the glucose glycoside is preferably at least one selected from the group consisting of octyl glucoside, decyl glucoside, dodecyl glucoside, tetradecyl glucoside, hexadecyl glucoside, and octadecyl glucoside.

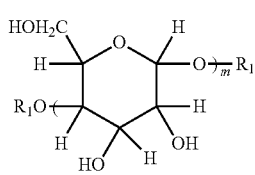

(1')

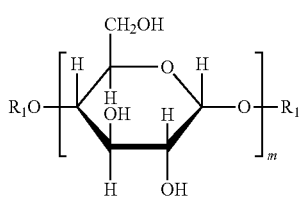

(11')

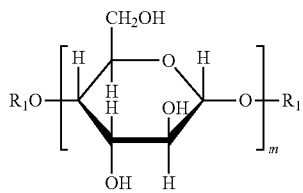

(12')

According to an embodiment of the present invention, in formula (1), two occurrences of $R_1$, same as or different from one another, are each independently selected from the group consisting of hydrogen and $C_{1-20}$ linear or branched alkyl group, preferably each independently selected from the group consisting of hydrogen and C5-20 linear or branched alkyl group, more preferably each independently selected from the group consisting of hydrogen and C8-18 linear or branched alkyl group, more preferably octyl, decyl, dodecyl, tetradecyl, hexadecyl or octadecyl. m is an integer of 1 to 3 or 2. * represents a bonding site of said substituent A or of said substituent B, provided that there are at least two said bonding sites. In other words, the glucose or glucose glycoside must be substituted with at least one substituent A and at least one substituent B.

According to an embodiment of the present invention, the aryl-substituted saccharide or glycoside is one or more compounds selected from the group consisting of compounds represented schematically by the following formula (I-1), formula (I-2), formula (I-3) and formula (I-4). In these formulae, all the substituents and numbers (for example, $R_1$, etc.) which are not explicitly defined apply directly to the corresponding definitions in formula (1), the substituent A and the substituent B as described above in the present description.

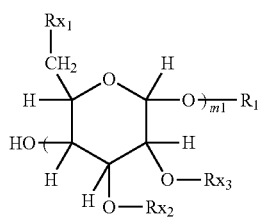

(I-1)

In formula (I-1), among the m1 number of $Rx_1$, one $Rx_1$ is the substituent A, and the remaining $Rx_1$, same as or different from each other, are each independently selected from the group consisting of the substituent A and hydroxyl group. m1 is an integer of 2 to 3. m1 number of $Rx_2$ and m1 number of $Rx_3$, same as or different from each other, are each independently selected from the group consisting of hydrogen atom and the substituent B, provided that at least one of these $Rx_2$ and $Rx_3$ is the substituent B.

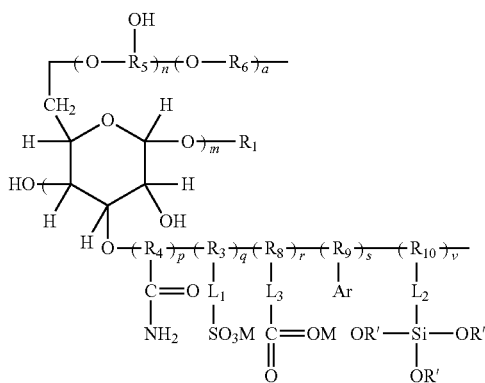

(I-2)

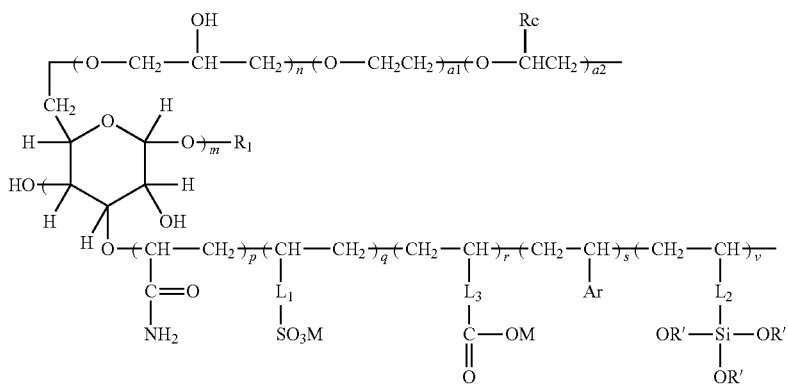

(I-3)

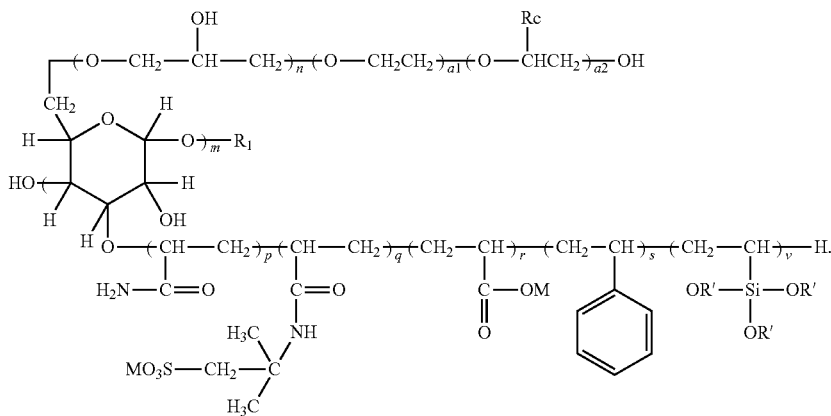

(I-4)

According to an embodiment of the invention, the amine value of the aryl-substituted saccharide or glycoside ranges generally from 0.10 to 0.80 mmol/g, preferably from 0.20 to 0.50 mmol/g.

According to an embodiment of the present invention, the aryl-substituted saccharide or glycoside can be produced according to the production process of the present invention. Accordingly, the invention also relates to a process for producing the aryl-substituted saccharide or glycoside or a mixture of a plurality of the aryl-substituted saccharides or glycosides, comprising the following steps 1) and 2).

Step 1): reacting a saccharide or glycoside (preferably an alkyl glycoside) represented schematically by the following formula (X-1) or formula (X-2) with an etherifying agent, optionally in the presence of a catalyst, to obtain an etherified saccharide or glycoside, (also called as a polyether alcohol-based alkyl glycoside). Here, it is preferable that the etherifying agent and the alkyl glycoside are reacted in the presence of an alkaline catalyst to obtain the polyether alcohol-based alkyl glycoside.

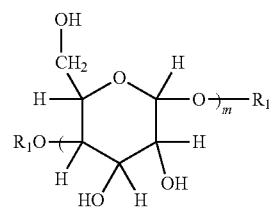

(X-1)

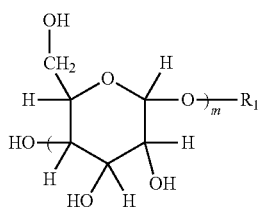
(X-2)

According to an embodiment of the present invention, in formula (X-1) and formula (X-2), two occurrences of $R_1$, same as or different from one another, are each independently selected from the group consisting of hydrogen and $C_{1-20}$ linear or branched alkyl group, preferably each independently selected from hydrogen and a C5-20 linear or branched alkyl group, more preferably each is independently selected from the group consisting of hydrogen and C8-18 linear or branched alkyl group, more preferably octyl group, decyl group, dodecyl group, tetradecyl group, hexadecyl group or octadecyl group. m is an integer of 1 to 3 or 2.

According to an embodiment of the present invention, in step 1), an alkylene oxide monomer schematically represented by the following formula (A-11), a polyhydroxyl monomer schematically represented by the following formula (A-21), or a combination thereof is preferably used as the etherifying agent.

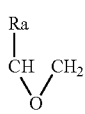
(A-11)

According to an embodiment of the present invention, in formula (A-11), Ra is a hydrogen atom or a $C_{1-5}$ linear or branched alkyl group, preferably a hydrogen atom or a $C_{1-3}$ linear or branched alkyl group.

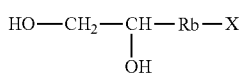
(A-21)

According to an embodiment of the present invention, in formula (A-21), Rb is a C1-4 linear or branched alkylenyl group or C1-2 linear or branched alkylenyl group, and X is a hydroxyl group or a halogen atom such as Cl or Br.

According to an embodiment of the present invention, in step 1), an alkaline catalyst is preferably used as the catalyst. Here, the alkaline catalyst is preferably selected from sodium carbonate, potassium carbonate, calcium oxide or magnesium oxide.

According to an embodiment of the present invention, in step 1), the etherifying agent is preferably selected from propylene oxide, 1,2-butylene oxide or 1,2-pentylene oxide.

According to an embodiment of the invention, in step 1), the alkyl glycoside is preferably selected from octyl glycoside, decyl glycoside, dodecyl glycoside, tetradecyl glycoside, hexadecyl glycoside or octadecyl glycoside.

According to an embodiment of the present invention, in step 1), the type and source of the alkyl glycoside are not particularly limited, and the alkyl glycoside may be those conventionally known to those skilled in the art or may be prepared by a process of producing alkyl glycoside known to those skilled in the art, or may be commercially obtained. For example, the alkyl glycoside of the present invention is provided by Henan Daochun Chemical Technology Co., Ltd.

According to an embodiment of the present invention, in step 1), the weight ratio of the etherifying agent, the saccharide or glycoside (such as the alkyl glycoside) and the catalyst is preferably 24:(70-100):(10-30), more preferably 24:(75-95):(15-25), most preferably 24:(80-90):20.

According to an embodiment of the present invention, the reaction in step 1) is preferably carried out under stirring. Here, the stirring speed used is generally 800-1200 r/min, preferably 900-1100 r/min, and most preferably 1000 r/min.

According to an embodiment of the present invention, the reaction in the step 1) is generally carried out at a temperature of 95-155° C., preferably 110-140° C., and most preferably 120-130° C.

According to an embodiment of the present invention, the reaction in the step 1) is generally carried out for 1 to 3 hours, preferably 1.5 to 2.5 hours, most preferably 2 hours.

Step 2): reacting the etherified saccharide or glycoside with an arylethylene monomer represented schematically by the following formula (B-11) or formula (B-12), optionally using an acrylamide monomer represented schematically by the following formula (B-21), optionally using a sulfoethylene monomer represented schematically by the following formula (B-31) or formula (B-32), optionally using a siloxyethylene monomer represented schematically by the following formula (B-41) or formula (B-42), and optionally using a carboxyethylene monomer represented schematically by the following formula (B-51) or formula (B-52) for the reaction, to obtain the aryl-substituted saccharide or glycoside. It is preferred here that the polyether alcohol-based alkyl glycoside, acrylic acid, styrene, acrylamide, 2-acrylamido-2-methylpropanesulfonic acid and optionally vinyltriethoxysilane are reacted under the action of an initiator to provide the aryl-substituted saccharide or glycoside.

(B-11)

According to an embodiment of the present invention, in formula (B-11), Ar is an optionally substituted C6-20 aryl group, preferably an optionally substituted phenyl group.

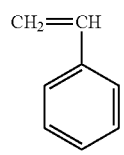
(B-12)

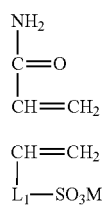
(B-21)

(B-31)

-continued

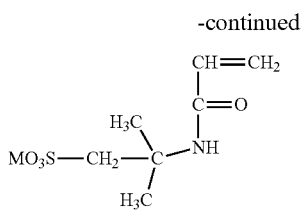
(B-32)

According to an embodiment of the present invention, in formula (B-31) and formula (B-32), $L_1$ is any linking group, preferably any linking group having no more than 10 carbon atoms, preferably a single bond, C2-10 linear or branched alkylenyl group, —C(═O)—C2-10 linear or branched alkylenyl group, —C(═O)O—C2-10 linear or branched alkylenyl group, —C(═O)NH—C2-10 linear or branched alkylenyl group, C2-5 linear or branched alkylenyl group-C(═O)—C2-5 linear or branched alkylenyl group, C2-5 linear or branched alkylenyl group-C(═O)O—C2-5 linear or branched alkylenyl group, or C2-5 linear or branched alkylenyl group-C(═O)NH—C2-5 linear or branched alkylenyl group, more preferably-C(═O)NH—C2-10 linear or branched alkylenyl group. M is hydrogen, alkali metal (such as K or Na) or ammonium ($NH_4$).

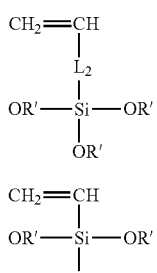

According to an embodiment of the present invention, in formula (B-41) and formula (B-42), $L_2$ is any linking group, preferably any linking group having no more than 10 carbon atoms, preferably a single bond or C2-10 linear or branched alkylenyl group, especially a single bond. R' is a C1-4 linear or branched alkyl group, preferably methyl or ethyl.

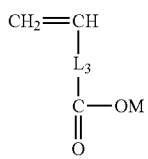
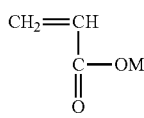

According to an embodiment of the present invention, in formula (B-51) and formula (B-52), $L_3$ is any linking group, preferably any linking group having no more than 10 carbon atoms, preferably a single bond or C2-10 linear or branched alkylenyl group, especially a single bond. M is hydrogen, alkali metal (such as K or Na) or ammonium ($NH_4$).

According to an embodiment of the invention, in step 2), a free-radical polymerization reaction is preferably carried out in the presence of an initiator.

According to an embodiment of the present invention, in step 2), the initiator may be any radical polymerization initiator, such as ammonium persulfate, potassium persulfate, cerium ammonium nitrate, azobisisobutyronitrile, dimethyl azobisisobutyrate, azobisisobutylamidine hydrochloride, or any combination thereof.

According to an embodiment of the present invention, in step 2), the weight ratio of the etherifying agent, the carboxyethylene monomer (such as acrylic acid), the arylethylene monomer (such as styrene), the acrylamide monomer (such as acrylamide), the sulfoethylene monomer (such as 2-acrylamido-2-methylpropanesulfonic acid), the siloxyethylene monomer (such as vinyltriethoxysilane), and the initiator is generally 24:(20-40):(20-40):(20-40):(10-20):(10-20):(0.6-1.8), preferably 24:(25-35):(25-35):(25-35):(12-18):(12-18):(0.8-1.6), most preferably 24:30:30:30:(14-16):(14-16):(1.0-1.4).

According to an embodiment of the present invention, the reaction in step 2) is preferably carried out under stirring. Here, the stirring speed is preferably 800-1200 r/min, more preferably 900-1100 r/min, and most preferably 1000 r/min.

According to an embodiment of the invention, the reaction in step 2) is preferably carried out at a temperature of 40 to 80° C., more preferably 50 to 70° C., most preferably 60° C.

According to an embodiment of the present invention, the reaction in step 2) is preferably carried out for 1 to 3 hours, more preferably 1.5 to 2.5 hours, most preferably 2 hours.

According to an embodiment of the present invention, the reaction in step 2) is preferably carried out under alkaline conditions, more preferably at a pH of 8 to 12, more preferably at a pH of 9 to 11, most preferably at a pH of 10. Accordingly, a pH adjustor is preferably added to the reaction system of said step 2) according to the present invention, to adjust the pH into such ranges. Here, the pH adjuster is preferably selected from sodium hydroxide, potassium hydroxide, or ammonia water.

According to an embodiment of the present invention, in the step 2), the weight ratio of the etherifying agent and the pH adjusting agent is generally 24:(18-40), preferably 24:(20-35), most preferably 24:(25-30).

According to an embodiment of the invention, there is also provided a drilling fluid composition. The drilling fluid composition comprises an aryl-substituted saccharide or glycoside according to any one of the preceding contents and a base slurry.

According to an embodiment of the invention, the aryl-substituted saccharide or glycoside is present in an amount of 0.1 to 5 wt %, preferably 0.5 to 1.5 wt % or 0.8 to 1.2 wt % or about 1 wt %, based on 100 wt % of the total weight of the drilling fluid composition.

According to an embodiment of the invention, there is also provided a process of producing the drilling fluid composition, comprising the step of mixing an aryl-substituted saccharide or glycoside with a base slurry. Here, the aryl-substituted saccharide or glycoside is an aryl-substituted saccharide or glycoside according to any of the preceding contents.

According to an embodiment of the present invention, the base slurry may be any base slurry known in the art, such as, in particular, a fresh water base slurry, a saturated brine base slurry, a composite brine base slurry or a calcareous soil base slurry.

According to an embodiment of the present invention, the components of the fresh water base slurry preferably comprise sodium carbonate, bentonite and water. Here, the weight content of the sodium carbonate in water is preferably 2 to 4 g/L, more preferably 2.5 to 3.5 g/L, most preferably 3 g/L; and the weight content of the bentonite in water is preferably 55-65 g/L, more preferably 58-62 g/L, and most preferably 60 g/L.

According to an embodiment of the invention, the components of the saturated brine base slurry preferably comprise a fresh water base slurry and NaCl. Here, the weight content of the NaCl in the fresh water base slurry is preferably 30 to 40%, more preferably 32 to 38%, and most preferably 34 to 36%.

According to an embodiment of the present invention, the components of the composite brine base slurry preferably comprise sodium chloride, magnesium chloride, calcium bentonite, sodium carbonate, and water. Here, the weight content of the sodium chloride in water is preferably 40 to 50 g/L, more preferably 42 to 48 g/L, most preferably 44 to 46 g/L. The weight content of the magnesium chloride in water is preferably 10-15 g/L, more preferably 11-14 g/L, and most preferably 12-13 g/L. The calcium chloride is preferably anhydrous calcium chloride. The weight content of the calcium chloride in water is preferably 4-6 g/L, more preferably 4.5-5.5 g/L, and most preferably 5 g/L. The weight content of the calcium bentonite in water is preferably 140-160 g/L, more preferably 145-155 g/L and most preferably 150 g/L. The sodium carbonate is preferably anhydrous sodium carbonate. The weight content of the sodium carbonate in water is preferably 8-10 g/L, more preferably 8.5-9.5 g/L, and most preferably 9 g/L.

According to an embodiment of the invention, the components of the calcareous soil base slurry preferably comprise sodium carbonate, calcium bentonite and water. Here, the sodium carbonate is preferably anhydrous sodium carbonate. The weight content of the sodium carbonate in water is preferably 0.003-0.007 g/mL, more preferably 0.004-0.006 g/L, and most preferably 0.005 g/L. The weight content of the calcium bentonite in water is preferably 0.05-0.15 g/mL, more preferably 0.08-0.12 g/mL, and most preferably 0.1 g/mL.

EXAMPLES

The present invention will be described in further detail below referring to examples and comparative examples, but the present invention is not limited thereto.

The raw materials used in the following examples and comparative examples were all commercially available products, wherein the alkyl glycoside of the present invention is provided by Henan Daochun Chemical Technology Co., Ltd Example 1

24 g propylene oxide, 70 g octyl glucoside, 10 g sodium carbonate were added into a four-necked flask equipped with condensation reflux and a stirring device, where the stirring rate was controlled at 800 r/min, and reacted at a temperature of 95° C. for 1 h, to provide a polyether alcohol-based octyl glucoside;

20 g of acrylic acid, 20 g of styrene, 20 g of acrylamide, and 10 g of 2-acrylamide-2-methylpropane sulfonic acid were added into the polyether alcohol-based octyl glucoside above, stirred at a stirring rate of 800 r/min, 18 g sodium hydroxide was used to adjust the pH of the reaction liquor to be 8, 0.6 g ammonium persulfate was added, and reacted at 40° C. for 1 h, to provide a red-brown transparent product (also called as an aryl-substituted glucoside component). The aryl-substituted saccharide or glucoside from example 1 had an amine value of 0.11 mmol/g.

The product prepared in example 1 of the present invention was subjected to an infrared spectrum detection, providing an infrared spectrogram as shown in FIG. 1. The detection results comprised: a peak at 3380 $cm^{-1}$ representing the stretching vibration of O—H bond, a peak at 2830-2950 $cm^{-1}$ representing the stretching vibration of C—H bond in methyl and methylene, which determined the presence of a glucoside structure; a peak at 1164 $cm^{-1}$ representing the stretching vibration of C—O—C bond, which determined the presence of a polyether structure; characteristic peaks of amido at 1689 $cm^{-1}$ and 1280 $cm^{-1}$; characteristic peaks of sulfonyl at 1171 $cm^{-1}$ and 987 $cm^{-1}$; a characteristic peak of carboxyl at 1418 $cm^{-1}$; and a characteristic peak of benzene ring at 1400-1600 $cm^{-1}$. It was determined that polyether group, amido group, sulfonyl group, carboxyl group and benzene ring group had been introduced into the molecular structure of the glucoside.

The process provided by example 1 of the present invention could produce a target product comprising the structure of formula 1:

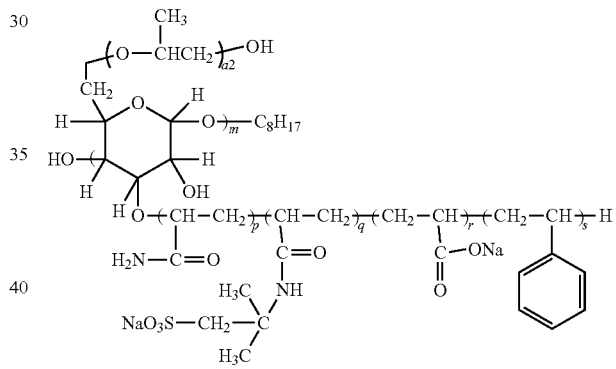

Formula 1

In formula 1, m is 1.4, a2 is 1, p is 12.8, q is 15.2, R is 14.9, and s is 11.6.

Example 2

24 g 1,2-butylene oxide, 80 g decyl glucoside, and 15 g potassium carbonate were added into a four-necked flask equipped with condensation reflux and a stirring device, where the stirring rate was controlled at 900 r/min, and reacted at a temperature of 100° C. for 2 h, to provide a polyether alcohol-based decyl glucoside;

30 g of acrylic acid, 30 g of styrene, 30 g of acrylamide, and 20 g of 2-acrylamide-2-methylpropane sulfonic acid were added into the polyether alcohol-based decyl glucoside above, stirred at a stirring rate of 900 r/min, 24 g potassium hydroxide was used to adjust the pH of the reaction liquor to be 9, 0.8 g potassium persulfate was added, and reacted at 50° C. for 2 h, to provide a red-brown transparent product. The aryl-substituted saccharide or glucoside from example 2 had an amine value of 0.23 mmol/g.

Figure 2:
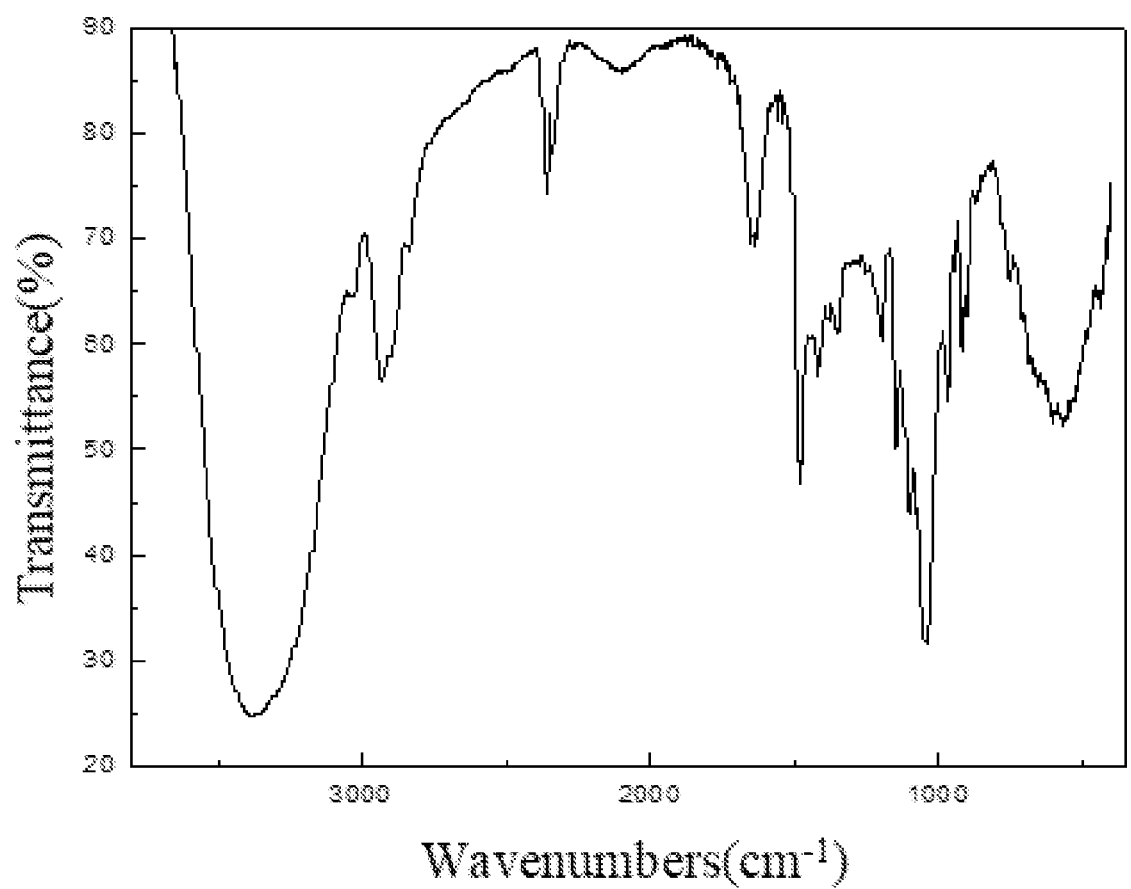
FIG. 2 is an infrared spectrum of an aryl-substituted saccharide or glycoside obtained in Example 2 of the present invention.

The product prepared in example 2 of the present invention was subjected to an infrared spectrum detection, providing an infrared spectrogram as shown in FIG. 2. The detection results comprised: a peak at 3381 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1165 cm$^{-1}$ representing the stretching vibration of C—O—C bond, which determined the presence of a polyether structure; characteristic peaks of amido group at 1687 cm$^{-1}$ and 1279 cm$^{-1}$; characteristic peaks of sulfonyl group at 1171 cm$^{-1}$ and 986 cm$^{-1}$; a characteristic peak of carboxyl at 1413 cm$^{-1}$; and a characteristic peak of benzene ring at 1400-1600 cm$^{-1}$. It was determined that polyether group, amido group, sulfonyl group, carboxyl group and benzene ring group had been introduced into the molecular structure of the glucoside.

The process provided by example 2 of the present invention could produce a target product comprising the structure of formula 2:

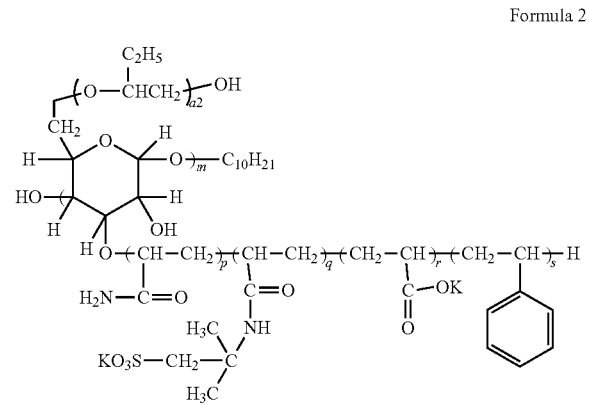

Formula 2

In formula 2, m is 1.8, a2 is 2, p is 15.5, q is 17.3, R is 16.8, and s is 13.2.

Example 3

24 g 1,2-pentylene oxide, 90 g dodecyl glucoside, and 20 g calcium oxide were added into a four-necked flask equipped with condensation reflux and a stirring device, where the stirring rate was controlled at 1000 r/min, and reacted at a temperature of 110° C. for 3 h, to provide a polyether alcohol-based dodecyl glucoside;

40 g of acrylic acid, 40 g of styrene, 40 g of acrylamide, and 20 g of 2-acrylamide-2-methylpropane sulfonic acid were added into the polyether alcohol-based dodecyl glucoside above, stirred at a stirring rate of 1000 r/min, 28 g aqueous ammonia was used to adjust the pH of the reaction liquor to be 10, 1.0 g ammonium ceric nitrate was added, and reacted at 60° C. for 3 h, to provide a red-brown transparent product. The aryl-substituted saccharide or glucoside from example 3 had an amine value of 0.38 mmol/g.

Figure 3:
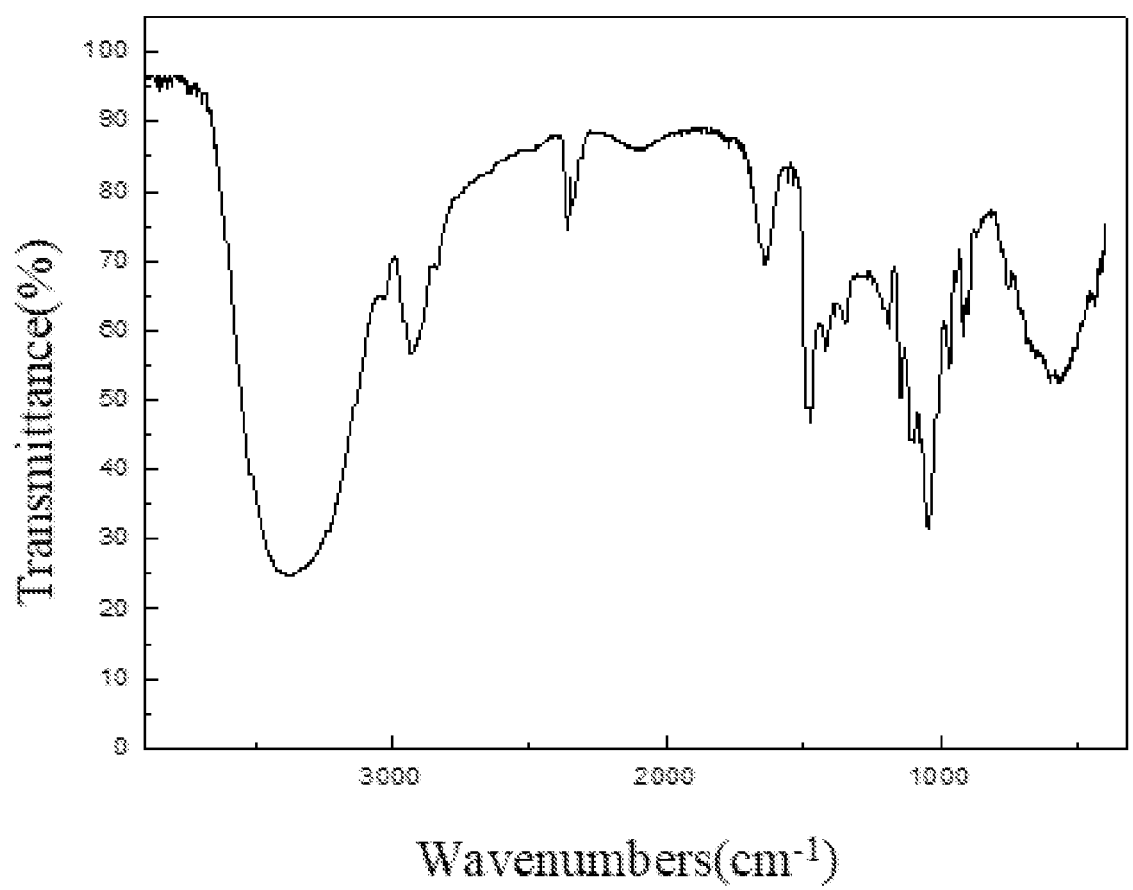
FIG. 3 is an IR spectrum of an aryl-substituted saccharide or glycoside obtained in Example 3 of the present invention.

The product prepared in example 3 of the present invention was subjected to an infrared spectrum detection, providing an infrared spectrogram as shown in FIG. 3. The detection results comprised: a peak at 3383 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1164 cm$^{-1}$ representing the stretching vibration of C—O—C bond, which determined the presence of a polyether structure;

characteristic peaks of amido group at 1686 cm$^{-1}$ and 1278 cm$^{-1}$; characteristic peaks of sulfonyl group at 1170 cm$^{-1}$ and 985 cm$^{-1}$; a characteristic peak of carboxyl at 1419 cm$^{-1}$; and a characteristic peak of benzene ring at 1400-1600 cm$^{-1}$. It was determined that polyether group, amido group, sulfonyl group, carboxyl group and benzene ring group had been introduced into the molecular structure of the glucoside.

The process provided by example 3 of the present invention could produce a target product comprising the structure of formula 3:

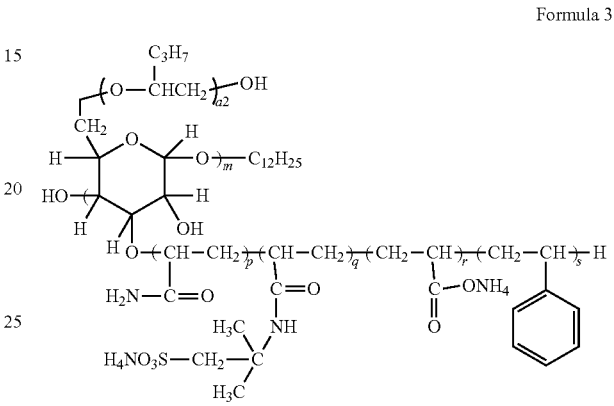

Formula 3

In formula 3, m is 2, a2 is 5, p is 16.6, q is 18.8, R is 18.9, and s is 13.1.

Example 4

24 g propylene oxide, 100 g myristyl glucoside, and 30 g magnesium oxide were added into a four-necked flask equipped with condensation reflux and a stirring device, where the stirring rate was controlled at 1100 r/min, and reacted at a temperature of 120° C. for 3 h, to provide a polyether alcohol-based myristyl glucoside;

40 g of acrylic acid, 40 g of styrene, 40 g of acrylamide, and 20 g of 2-acrylamide-2-methylpropane sulfonic acid were added into the polyether alcohol-based myristyl glucoside above, stirred at a stirring rate of 1100 r/min, 32 g sodium hydroxide was used to adjust the pH of the reaction liquor to be 11, 1.2 g azodiisobutyronitrile was added, and reacted at 70° C. for 3 h, to provide a red-brown transparent product. The aryl-substituted saccharide or glucoside from example 4 had an amine value of 0.42 mmol/g.

Figure 4:
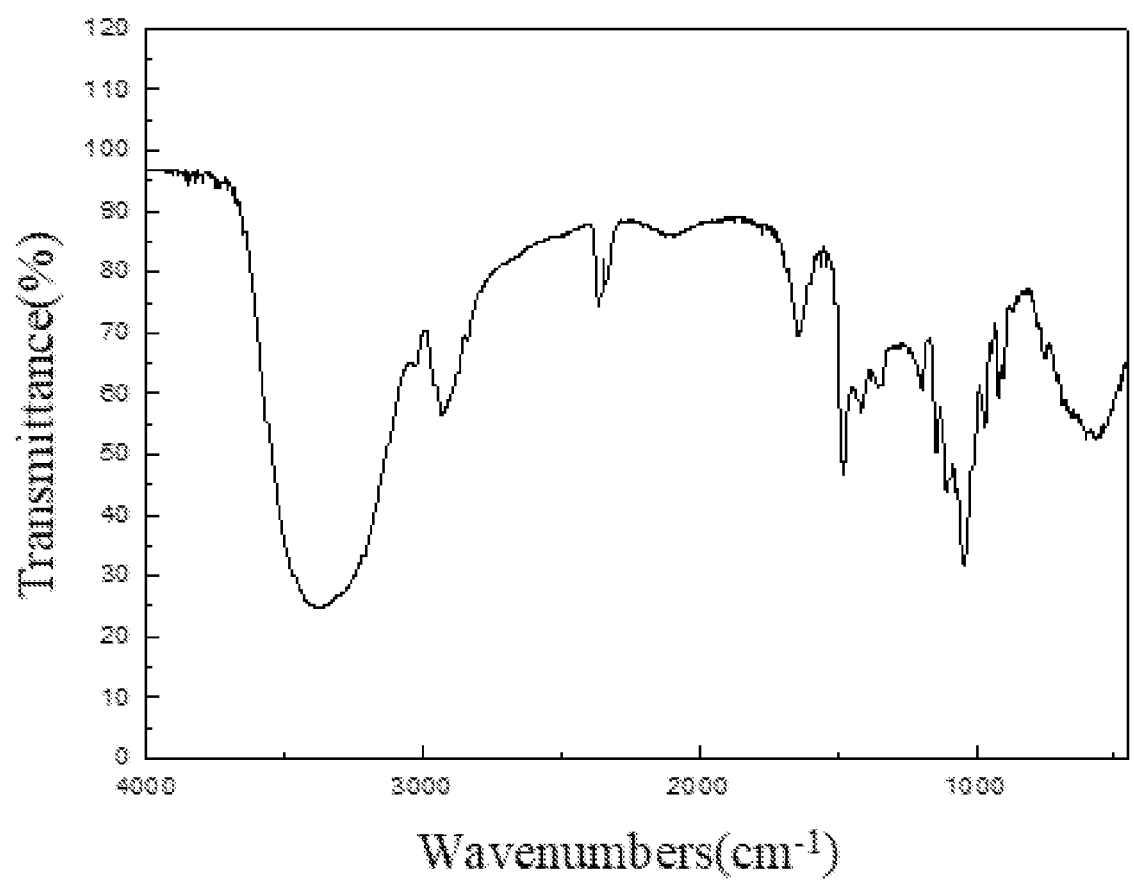
FIG. 4 is an IR spectrum of an aryl-substituted saccharide or glycoside obtained in Example 4 of the present invention.

The product prepared in example 4 of the present invention was subjected to an infrared spectrum detection, providing an infrared spectrogram as shown in FIG. 4. The detection results comprised: a peak at 3382 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1166 cm$^{-1}$ representing the stretching vibration of C—O—C bond, which determined the presence of a polyether structure; characteristic peaks of amido group at 1687 cm$^{-1}$ and 1279 cm$^{-1}$; characteristic peaks of sulfonyl group at 1177 cm$^{-1}$ and 989 cm$^{-1}$; a characteristic peak of carboxyl at 1408 cm$^{-1}$; and a characteristic peak of benzene ring at 1400-1600 cm$^{-1}$. It was determined that polyether group, amido group, sulfonyl group, carboxyl group and benzene ring group had been introduced into the molecular structure of the glucoside.

The process provided by example 4 of the present invention could produce a target product comprising the structure of formula 4:

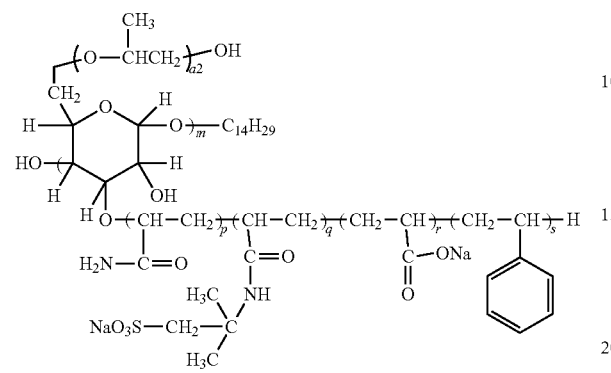

Formula 4

In formula 4, m is 1.4, a2 is 8, p is 17.3, q is 18.9, R is 19.2, and s is 13.5.

Example 5

24 g propylene oxide, 100 g cetyl glucoside, and 30 g sodium carbonate were added into a four-necked flask equipped with condensation reflux and a stirring device, where the stirring rate was controlled at 1200 r/min, and reacted at a temperature of 130° C. for 3 h, to provide a polyether alcohol-based cetyl glucoside;

40 g of acrylic acid, 40 g of styrene, 40 g of acrylamide, and 20 g of 2-acrylamide-2-methylpropane sulfonic acid were added into the polyether alcohol-based cetyl glucoside above, stirred at a stirring rate of 1200 r/min, 36 g sodium hydroxide was used to adjust the pH of the reaction liquor to be 12, 1.6 g dimethyl azodiisobutyrate was added, and reacted at 80° C. for 3 h, to provide a red-brown transparent product. The aryl-substituted saccharide or glucoside from example 5 had an amine value of 0.44 mmol/g.

Figure 5:
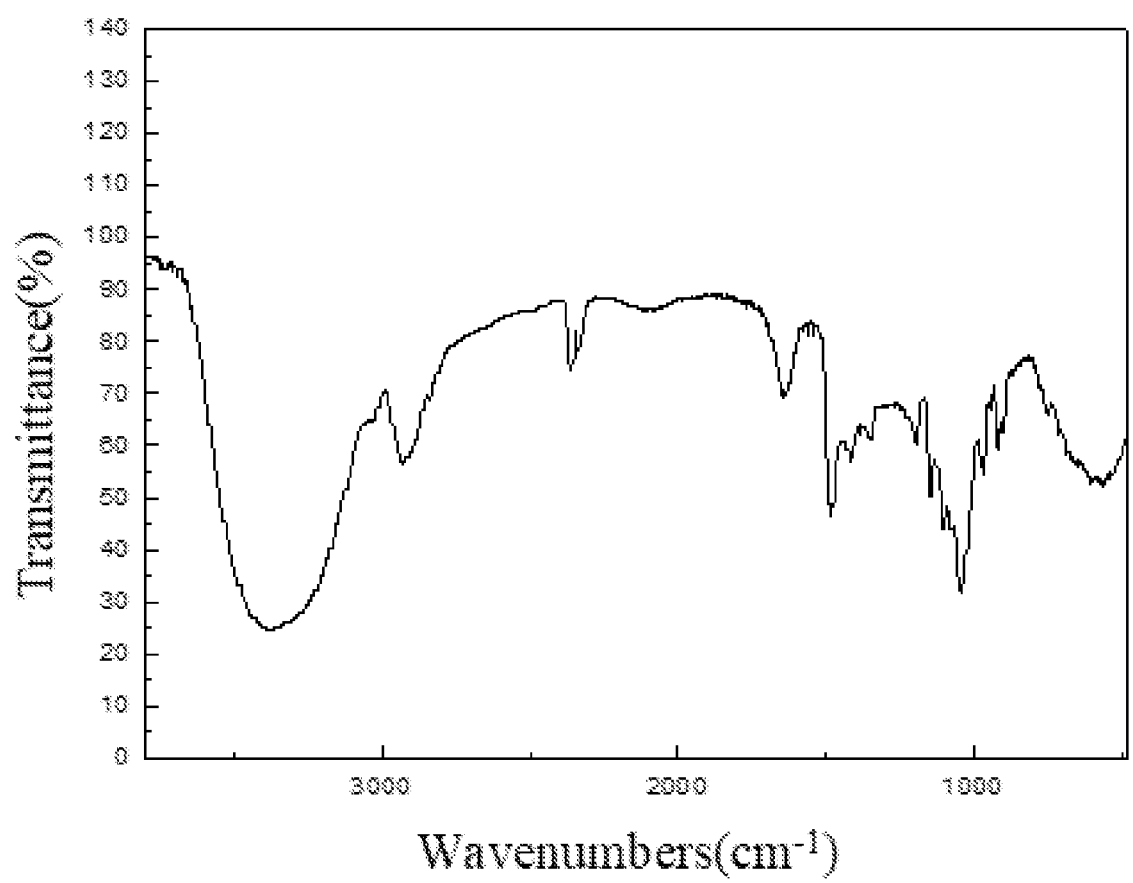
FIG. 5 is an IR spectrum of an aryl-substituted saccharide or glycoside obtained in Example 5 of the present invention.

The product prepared in example 5 of the present invention was subjected to an infrared spectrum detection, providing an infrared spectrogram as shown in FIG. 5. The detection results comprised: a peak at 3371 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1159 cm$^{-1}$ representing the stretching vibration of C—O—C bond, which determined the presence of a polyether structure; characteristic peaks of amido group at 1697 cm$^{-1}$ and 1263 cm$^{-1}$; characteristic peaks of sulfonyl group at 1147 cm$^{-1}$ and 962 cm$^{-1}$; a characteristic peak of carboxyl at 1411 cm$^{-1}$; and a characteristic peak of benzene ring at 1400-1600 cm$^{-1}$. It was determined that polyether group, amido group, sulfonyl group, carboxyl group and benzene ring group had been introduced into the molecular structure of the glucoside.

The process provided by example 5 of the present invention could produce a target product comprising the structure of formula 5:

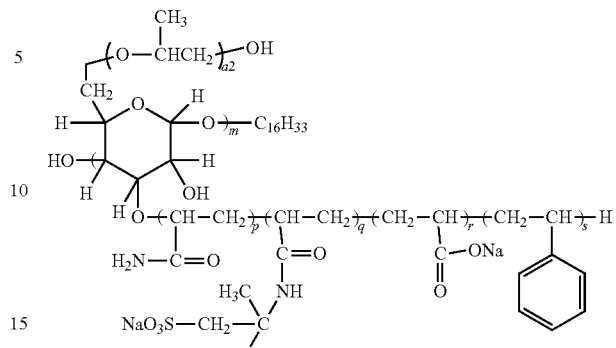

Formula 5

In formula 5, m is 1.4, a2 is 8, p is 18.6, q is 19.5, R is 20.2, and s is 13.8.

Example 6

24 g propylene oxide, 100 g stearyl glucoside, and 30 g potassium carbonate were added into a four-necked flask equipped with condensation reflux and a stirring device, where the stirring rate was controlled at 1200 r/min, and reacted at a temperature of 155° C. for 3 h, to provide a polyether alcohol-based stearyl glucoside;

40 g of acrylic acid, 40 g of styrene, 40 g of acrylamide, and 20 g of 2-acrylamide-2-methylpropane sulfonic acid were added into the polyether alcohol-based stearyl glucoside above, stirred at a stirring rate of 1200 r/min, 40 g potassium hydroxide was used to adjust the pH of the reaction liquor to be 12, 1.8 g azo diisobutyl amidine hydrochloride was added, and reacted at 80° C. for 3 h, to provide a red-brown transparent product. The aryl-substituted saccharide or glucoside from example 6 had an amine value of 0.56 mmol/g.

Figure 6:
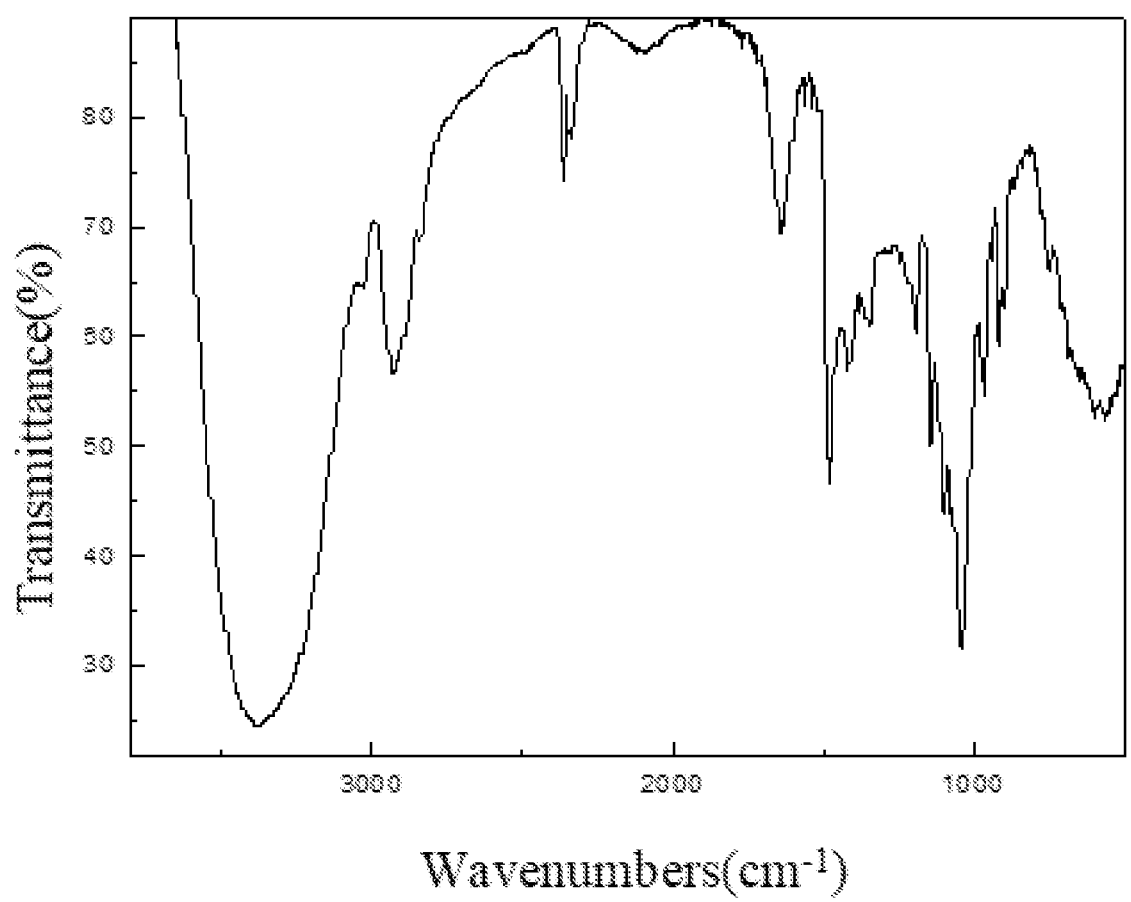
FIG. 6 is an IR spectrum of an aryl-substituted saccharide or glycoside obtained in Example 6 of the present invention.

The product prepared in example 6 of the present invention was subjected to an infrared spectrum detection, providing an infrared spectrogram as shown in FIG. 6. The detection results comprised: a peak at 3378 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1155 cm$^{-1}$ representing the stretching vibration of C—O—C bond, which determined the presence of a polyether structure; characteristic peaks of amido group at 1696 cm$^{-1}$ and 1210 cm$^{-1}$; characteristic peaks of sulfonyl group at 1146 cm$^{-1}$ and 963 cm$^{-1}$; a characteristic peak of carboxyl at 1407 cm$^{-1}$; and a characteristic peak of benzene ring at 1400-1600 cm$^{-1}$. It was determined that polyether group, amido group, sulfonyl group, carboxyl group and benzene ring group had been introduced into the molecular structure of the glucoside.

The process provided by example 6 of the present invention could produce a target product comprising the structure of formula 6:

Formula 6

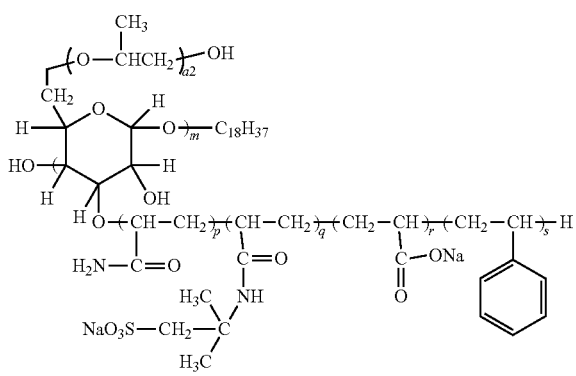

In formula 6, m is 1.4, a2 is 10, p is 19.7, q is 19.9, R is 22.5, and s is 14.7.

Example 7

24 g propylene oxide, 100 g stearyl glucoside, and 30 g sodium carbonate were added into a four-necked flask equipped with condensation reflux and a stirring device, where the stirring rate was controlled at 1200 r/min, and reacted at a temperature of 155° C. for 3 h, to provide a polyether alcohol-based stearyl glucoside;

40 g of acrylic acid, 40 g of styrene, 40 g of acrylamide, and 20 g of 2-acrylamide-2-methylpropane sulfonic acid, and 20 g of vinyl triethoxy silane were added into the polyether alcohol-based stearyl glucoside above, stirred at a stirring rate of 1200 r/min, 40 g sodium hydroxide was used to adjust the pH of the reaction liquor to be 12, 1.8 g ammonium persulfate was added, and reacted at 80° C. for 3 h, to provide a red-brown transparent product. The aryl-substituted saccharide or glucoside from example 7 had an amine value of 0.62 mmol/g.

Figure 7:
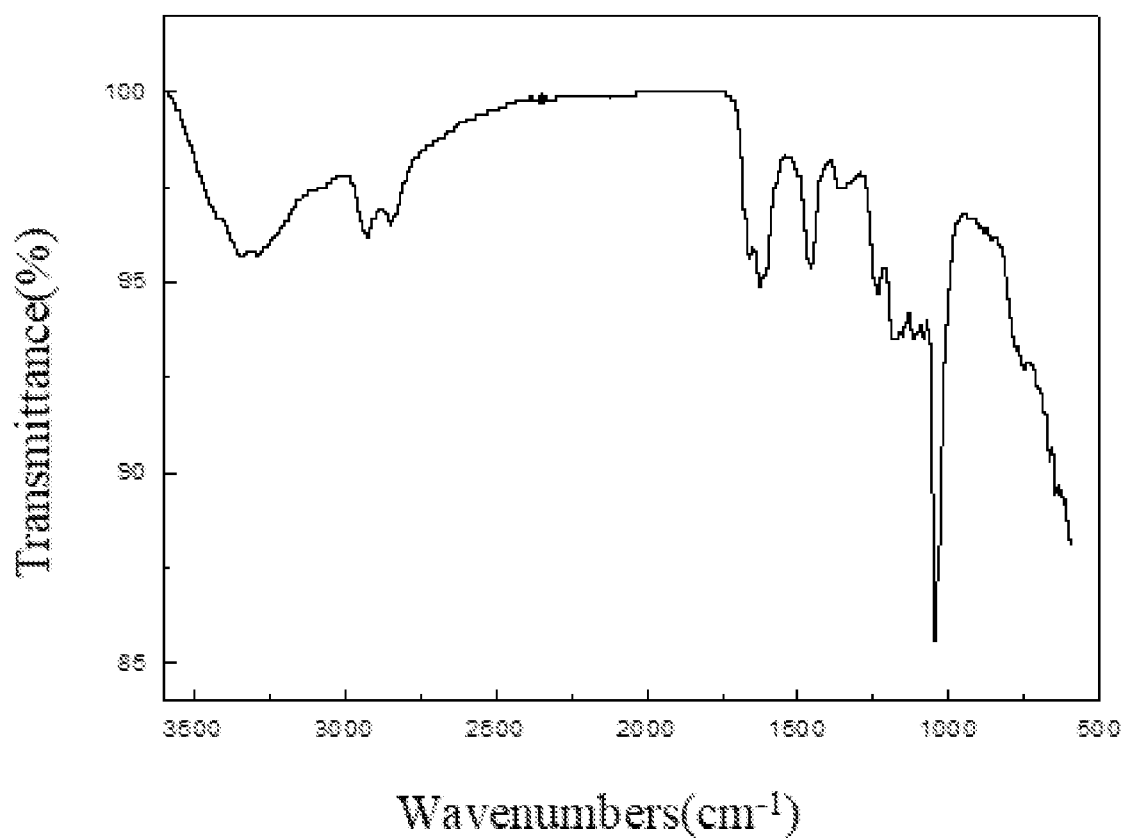
FIG. 7 is an IR spectrum of an aryl-substituted saccharide or glycoside obtained in Example 7 of the present invention.

The product prepared in example 7 of the present invention was subjected to an infrared spectrum detection, providing an infrared spectrogram as shown in FIG. 7. The detection results comprised: a peak at 3339 cm$^{-1}$ representing the stretching vibration of O—H bond, a peak at 2830-2950 cm$^{-1}$ representing the stretching vibration of C—H bond in methyl and methylene, which determined the presence of a glucoside structure; a peak at 1153 cm$^{-1}$ representing the stretching vibration of C—O—C bond, which determined the presence of a polyether structure; characteristic peaks of amido group at 1686 cm$^{-1}$ and 1238 cm$^{-1}$; characteristic peaks of sulfonyl group at 1112 cm$^{-1}$ and 942 cm$^{-1}$; a characteristic peak of carboxyl at 1408 cm$^{-1}$; a characteristic peak of silica group at 1400-1600 cm$^{-1}$; and a characteristic peak of siloxy at 1044 cm$^{-1}$ and 1108 cm$^{-1}$. It was determined that polyether group, amido group, sulfonyl group, carboxyl group, benzene ring group and siloxy group had been introduced into the molecular structure of the glucoside.

The process provided by example 7 of the present invention could produce a target product comprising the structure of formula 7:

Formula 7

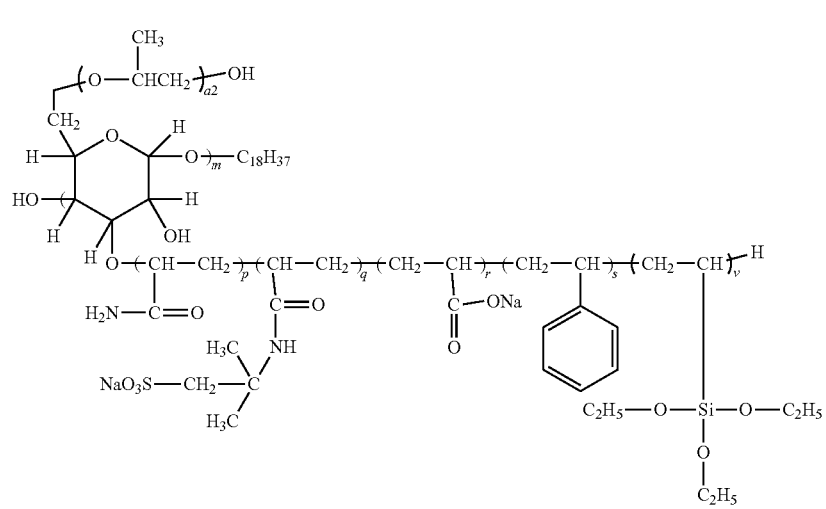

In formula 7, m is 1.4, a2 is 12, p is 19.7, q is 19.9, R is 22.5, s is 14.7, and v is 12.5.

Example 8

The products produced from examples 1-7 of the present invention were added respectively into 350 mL of saturated brine base slurry to form a drilling fluid, with a weight concentration of the product in the drilling fluid of 1%, for which the saturated brine base slurry was produced by: adding 3 g anhydrous sodium carbonate and 60 g bentonite into 1 L water, stirring for 20 min and standing at room temperature for 24 h, to obtain a fresh water base slurry; adding NaCl into the fresh water base slurry to have a weight content of NaCl in the fresh water base slurry of 36%, stirring at a high speed for 20 min, and standing at room temperature for 24 h, to obtain the saturated brine base slurry. According to the standard method provided in GB/T16783.1-2014, "Petroleum and natural gas industries-Field testing of drilling fluids-Part 1: Water-based fluids", the filtration loss reducing property of the drilling fluid was tested after a hot rolling for 16 hours at a high temperature of 240° C., the detection results as shown in Table 1.

TABLE 1 the filtration loss reducing property of the products produced according to examples 1-7 of the present invention against the saturated brine

|  | FL/ mL | Filtration loss reducing rate/% | pH |
|---|---|---|---|
| Saturated brine base slurry | 142.0 | — | 9 |
| Saturated brine base slurry + 1.0% example 1 | 20.1 | 85.85 | 9 |
| Saturated brine base slurry + 1.0% example 2 | 19.9 | 85.99 | 9 |
| Saturated brine base slurry + 1.0% example 3 | 19.7 | 86.13 | 9 |
| Saturated brine base slurry + 1.0% example 4 | 18.5 | 86.97 | 9 |
| Saturated brine base slurry + 1.0% example 5 | 18.1 | 87.25 | 9 |
| Saturated brine base slurry + 1.0% example 6 | 17.2 | 87.89 | 9 |
| Saturated brine base slurry + 1.0% example 7 | 16.4 | 88.45 | 9 |

(conditions for the hot rolling comprise: 240° C., 16 h; and FL represents medium-pressure filtration loss)

It could be seen from Table 1 that: after 16 h of hot rolling at 240° C., by adding 1% of the product into 350 mL of the saturated brine base slurry, the medium pressure filtration loss was reduced from 142.0 mL to 16.4-20.1 mL, with a filtration loss reducing rate of 85.85-88.45%, compared with the composite brine without addition of the product, where the product could still reduce significantly the filtration loss of the drilling fluid even after being polluted with the saturated brine, which meant a good filtration loss reducing property against high temperature and against saturated brine.

Example 9

The filtration loss reducing property of the products produced by examples 1-7 of the present invention were tested according to the method described in example 8, except that, the saturated brine base slurry was replaced with composite brine base slurry; in which the composite brine base slurry was produced by adding 45 g sodium chloride, 13 g magnesium chloride and 5 g anhydrous calcium chloride into 1 L water, dissolving sufficiently, followed by adding 150 g of calcium bentonite and 9 g of anhydrous sodium carbonate, stirring at a high speed for 20 min, and standing at room temperature for 24 h, to obtain the composite brine base slurry. The detection results were showed in Table 2.

TABLE 2 the filtration loss reducing property of the products produced according to examples 1-7 of the present invention against the composite salt

|  | FL/ mL | Filtration loss reducing rate/% | pH |
|---|---|---|---|
| Composite brine base slurry | 110.0 | — | 9 |
| Composite brine base slurry + 1.0% Example 1 | 10.8 | 90.18 | 9 |
| Composite brine base slurry + 1.0% Example 2 | 10.2 | 90.73 | 9 |
| Composite brine base slurry + 1.0% Example 3 | 9.6 | 91.27 | 9 |
| Composite brine base slurry + 1.0% Example 4 | 9.4 | 91.45 | 9 |
| Composite brine base slurry + 1.0% Example 5 | 8.8 | 92.00 | 9 |
| Composite brine base slurry + 1.0% Example 6 | 8.8 | 92.00 | 9 |
| Composite brine base slurry + 1.0% Example 7 | 8.8 | 92.00 | 9 |

(Conditions for the hot rolling comprise: 240° C., 16 h; and FL represents medium-pressure filtration loss)

It could be seen from Table 2 that: after 16 h of hot rolling at 240° C., by adding 1% of the product into 350 mL of the composite brine base slurry, the medium pressure filtration loss was reduced from 110 mL to 8.8-10.8 mL, with a filtration loss reducing rate of 90.18-92%, compared with the composite brine without addition of the product, where the product could still reduce significantly the filtration loss of the drilling fluid even after being polluted with the composite brine, which meant a good filtration loss reducing property against high temperature and against composite brine.

Example 10

The products of the present invention were formulated into aqueous solutions at a weight concentration of 1%, rolled at a high temperature of 240° C. for 16 h, and tested for the primary shale recovery and relative shale recovery according to the following method:

Aqueous solutions of the products with a weight concentration of 1% were stirred at a high speed of 7000 rpm for 5 min, and poured into an aging tank for later use. Rock debris at 2.0 mm-5.0 mm was dried at 103° C. for 4 h, and cooled to room temperature, after which $G_0$ g of the rock debris was weighed and put into the aging tank to be rolled with the drilling fluid in the aging tank for 16 h at 240° C., cooled, and taken out. The rock debris was recovered using a sieve with a pore diameter of 0.42 mm, dried at 103° C. for 4 h, cooled to room temperature, and weighed for the weight of the rock debris recovered, which was recorded as $G_1$. The weighed rock debris recovered was then put into clear water, rolled for 16 hours at 240° C., cooled and taken out. The rock debris was recovered using a sieve with a pore diameter of 0.42 mm, dried for 4 hours at 103° C., cooled to room temperature, and weighed for the weight of the rock debris recovered, which was recorded as $G_2$. The primary shale recovery rate, the secondary shale recovery rate and relative shale recovery rate:

Primary shale recovery rate=$G_1/G_0 \times 100\%$;

Secondary shale recovery rate=$G_2/G_0 \times 100\%$;

Relative shale recovery rate=secondary shale recovery rate/primary shale recovery rate$\times 100\%$;

The products produced from Examples 1 to 7 of the invention were respectively produced into aqueous solutions of products with a weight concentration of 1%, and were rolled for 16 hours at 240° C. using the method above, so as to determine the primary shale recovery rate and the relative shale recovery rate. The results were shown in Table 3.

TABLE 3 test results of shale recovery for products produced in examples 1-7 of the present invention

| Ex. | Conditions for rolling at a high temperature | Primary shale recovery rate/% | Relative shale recovery rate/% |
|---|---|---|---|
| 1 | 240° C., 16 h | 95.54 | 98.87 |
| 2 | 240° C., 16 h | 95.67 | 98.99 |
| 3 | 240° C., 16 h | 96.78 | 99.54 |
| 4 | 240° C., 16 h | 96.85 | 99.76 |
| 5 | 240° C., 16 h | 96.99 | 99.88 |
| 6 | 240° C., 16 h | 97.21 | 99.90 |
| 7 | 240° C., 16 h | 97.83 | 99.94 |

It could be seen from Table 3 that, by immersing shale with the products at a weight concentration of 1%, after rolling at 240° C. for 16 hours, the primary shale recovery rates were more than 95%, and the relative shale recovery rates were more than 98%, showing good high temperature resistance and strong inhibition performance.

Example 11

The products produced in examples 1 to 7 of the present invention were formulated into aqueous solutions having 3 wt % of the product, respectively, and the extreme pressure lubrication coefficients were measured at room temperature. The measurement method was as follows: immersing the slider of the instrument into the aqueous solutions having 3 wt % of the product, adjusting the value of a torque wrench to be 16.95 N/m, and operating the instrument for 5 min, to read the numerical value X displayed on the instrument when the slider was immersed in the aqueous solutions having 3 wt % of the product; and immersing the slider of the instrument into clear water, adjusting the value of the torque wrench to be 16.95 N/m, and operating the instrument for 5 min, to read the numerical value Y displayed on the instrument when the slider was immersed in the clear water, wherein the formula for the calculation of the extreme pressure lubrication coefficient was as follows $$K = \frac{X \times 34}{Y \times 100};$$

In the above formula: k denoted the extreme pressure lubrication coefficient; X denoted the numerical value displayed on the instrument when the sliding block was immersed in the aqueous solutions having 3 wt % of the product; and Y denoted a numerical value displayed on the instrument when the sliding block was immersed in clear water.

According to GB/T16783.1-2014, "Petroleum and natural gas industries-Field testing of drilling fluids-Part 1: Water-based fluids" the compatibilities of the products produced in examples 1-7 of the present invention were tested.

The biotoxicity $EC_{50}$ values of the products produced in examples 1-7 of the present invention were tested as follows: adding the products produced according to the present invention into a solution of sodium chloride at a weight concentration of 3%, formulating respectively into 10 mL of sample solutions to be tested at 0 mg·dm$^{-3}$, 5000 mg·dm$^{-3}$, 10000 mg·dm$^{-3}$, 25000 mg·dm$^{-3}$, 50000 mg·dm$^{-3}$ and 100000 mg·dm$^{-3}$, and standing for 60 min; and adding sequentially 10 mg of luminous bacteria T3 powder into the sample solutions to be detected, fully shaking and uniformly mixing, and determining respectively the biotoxicity $EC_{50}$ values 15 min after the luminous bacteria being contacted with the sample solution to be detected, with taking a sodium chloride solution at a weight concentration of 3% as a control.

The products produced in examples 1 to 7 of the present invention were produced into aqueous solutions having 3 wt % of the product, respectively, and the lubrication coefficients thereof were measured according to the above-described test methods; and the compatibility and biotoxicity $EC_{50}$ values were tested according to the above test methods, and the test results were shown in Table 4.

TABLE 4

Test results of lubricity, compatibility and biotoxicity of the products produced in examples 1-7 of the present invention

| Ex. | Extreme pressure lubrication coefficient | Reduction rate in lubrication coefficient/% | $EC_{50}$ value/ mg/L | Compatibility with conventional water-based drilling fluid |
|---|---|---|---|---|
| clear water | 0.340 | — | — | — |
| 1 | 0.074 | 78.24 | 539200 | compounded in any proportion |
| 2 | 0.069 | 79.71 | 542700 | compounded in any proportion |
| 3 | 0.062 | 81.76 | 547500 | compounded in any proportion |
| 4 | 0.068 | 80.00 | 546400 | compounded in any proportion |
| 5 | 0.062 | 81.76 | 548300 | compounded in any proportion |
| 6 | 0.064 | 81.18 | 543900 | compounded in any proportion |
| 7 | 0.062 | 81.76 | 544500 | compounded in any proportion |

It could be seen from Table 4 that the lubrication coefficients of the products of the invention at a weight concentration of 3% were <0.08, and the reduction rates in lubrication coefficients were >78%, representing good lubricating performances. The products of the invention and the conventional water-based drilling fluid could be compounded in any proportion, representing good compatibility. The products of the invention had $EC_{50}$ values >530000 mg/L, which were much larger than the emission standard of 30000 mg/L, representing no biotoxicity, and being green and environment-friendly.

The experiment results showed that, after a hot rolling for 16 hours at a temperature of 240° C., when the aryl-substituted saccharide or glucoside was added into saturated brine base slurry at a concentration of 1 wt %, the reduction rate of the API filtration loss was >85%; when the aryl-substituted saccharide or glucoside was added into composite brine base slurry, the reduction rate of the API filtration loss was >90%. After a hot rolling for 16 hours at a temperature of 240° C., the aqueous solution of the aryl-substituted saccharide or glycoside at a concentration of 1 wt % of the invention showed a primary shale recovery rate of >95% and a relative shale recovery rate of >98%. The aqueous solution of the aryl-substituted saccharide or glycoside at a concentration of 3 wt % according to the invention showed a lubricating coefficient of <0.08.

The invention claimed is:
1. An aryl-substituted saccharide or glycoside or a mixture of a plurality of aryl-substituted saccharides or glyco- sides, individually or in combination, bearing a substituent A and a substituent B, wherein the substituent A contains in its structure a unit

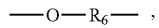, wherein $R_6$ is C2-8 linear or branched alkylene, the substituent B contains in its structure a unit

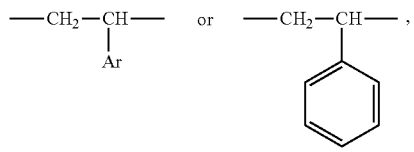, wherein Ar is an optionally substituted C6-20 aryl.

2. The aryl-substituted saccharide or glycoside or the mixture of a plurality of aryl-substituted saccharides or glycosides according to claim 1, wherein the substituent A further contains in its structure a unit

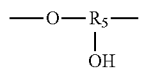

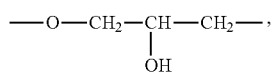, wherein $R_5$ is a C3-6 linear or branched trivalent alkyl group, and/or the substituent B further contains in its structure at least one group selected from a group

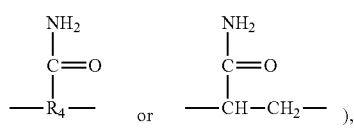, a group —$SO_3M$

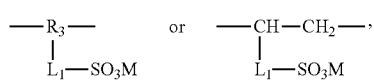,

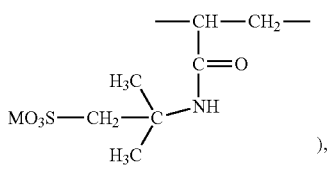

a unit

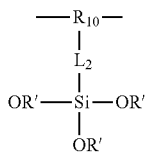

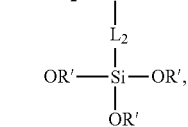,

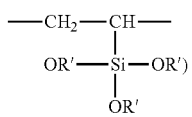

and a group —COOM

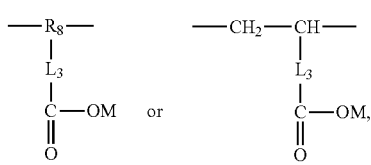

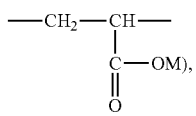,

M is hydrogen, an alkali metal, or ammonium ($NH_4$), $R_{10}$ is $C_{2-6}$ linear or branched alkylene, $L_2$ is any linking group having no more than 10 carbon atoms, $L_3$ is any linking group having no more than 10 carbon atoms, R' is C1-4 linear or branched alkyl.

3. The aryl-substituted saccharide or glycoside or the mixture of a plurality of aryl-substituted saccharides or glycosides according to claim 1, wherein the saccharide or glycoside is a glucose residue or a glucose glycoside residue represented schematically by the following formula (1),

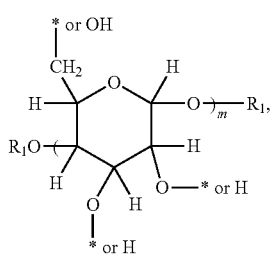  (1)

in formula (1), two occurrences of $R_1$, same as or different from one another, are each independently selected from the group consisting of hydrogen and C1-20 linear or branched alkyl group, m is an integer of 1-3, and * represents the bonding point of the substituent A or the substituent B, provided that there are at least two of the bonding points.

4. The aryl-substituted saccharide or glycoside or the mixture of a plurality of aryl-substituted saccharides or glycosides according to claim 1, having an amine value of from 0.10 to 0.80 mmol/g.

5. The aryl-substituted saccharide or glycoside or the mixture of a plurality of aryl-substituted saccharides or glycosides according to claim 1, wherein $R_6$ is C2-6 linear or branched alkylene, and/or Ar is optionally substituted phenyl.

6. The aryl-substituted saccharide or glycoside or the mixture of a plurality of aryl-substituted saccharides or glycosides according to claim 2, wherein $R_5$ is trivalent propyl or trivalent butyl, and/or the group

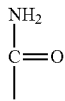

is a unit

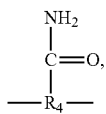

and/or the group-$SO_3M$ is a unit

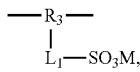

and/or, the unit

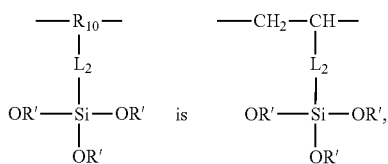

and/or the group —COOM is a unit

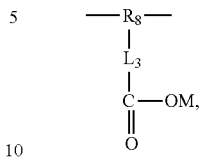

and/or $R_4$ is a C2-6 linear or branched alkylenyl group, and/or $R_3$ is a C2-6 linear or branched alkylenyl group, and/or $L_1$ is any linking group having no more than 10 carbon atoms, and/or $R_{10}$ is ethylene or propylene group, and/or $L_2$ is a single bond or C2-10 linear or branched alkylene, and/or $L_3$ is any linking group having no more than 10 carbon atoms, and/or R' is methyl or ethyl, and/or $R_8$ is C2-6 linear or branched alkylene.

7. The aryl-substituted saccharide or glycoside or the mixture of a plurality of aryl-substituted saccharides or glycosides according to claim 6, wherein the unit

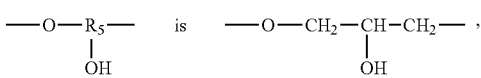

and/or the group

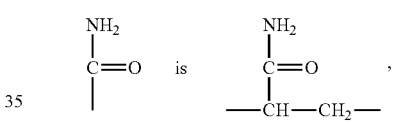

and/or the group-$SO_3M$ is

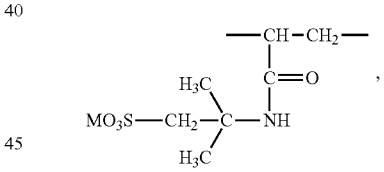

and/or the unit

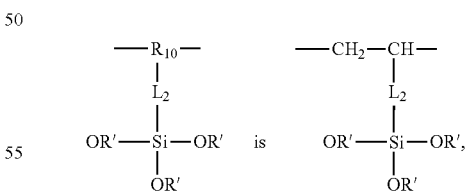

and/or the group —COOM is

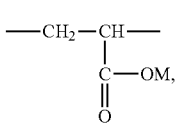

and/or the unit

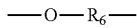

is selected from

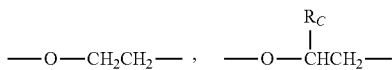

or any combination thereof, wherein Rc is C1-5 linear or branched alkyl, and/or $R_4$ is ethylene or propylene group, and/or $R_3$ is ethylene or propylene group, and/or $L_1$ is selected from a single bond, C2-10 linear or branched alkylene, —C(=O) —C2-10 linear or branched alkylene, —C(=O)O-C2-10 linear or branched alkylene, —C(=O)NH-C2-10 linear or branched alkylene, C2-5 linear or branched alkylene-C(=O)-C2-5 linear or branched alkylene, C2-5 linear or branched alkylene-C(=O)O—C2-5 linear or branched alkylene, and C2-5 linear or branched alkylene-C(=O)NH-C2-5 linear or branched alkylene, and/or $L_3$ is a single bond or C2-10 linear or branched alkylene, and/or $R_8$ is ethylene or propylene group.

8. The aryl-substituted saccharide or glycoside or the mixture of a plurality of aryl-substituted saccharides or glycosides according to claim 7, wherein the substituent A is represented schematically by the following formula (A-1), formula (A-2) or formula (A-3),

(A-1)

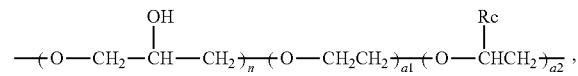
(A-2)
and

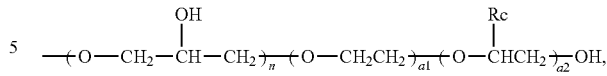
(A-3)

in these formulae, n is a number ranging from 0 to 10, a is a number ranging from 1 to 20, a1 is a number ranging from 0 to 20, a2 is a number ranging from 1 to 20, the substituent B is represented schematically by the following formula (B-1), formula (B-2) or formula (B-3),

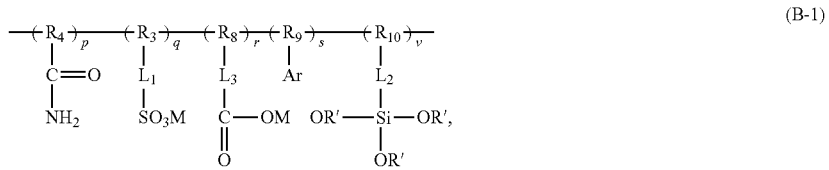
(B-1)

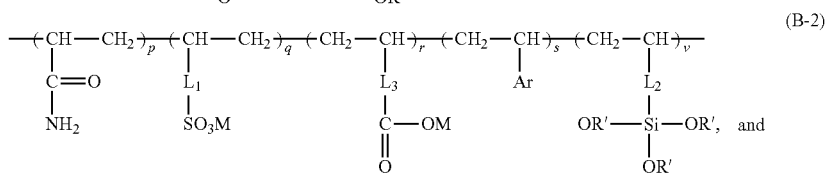
(B-2)

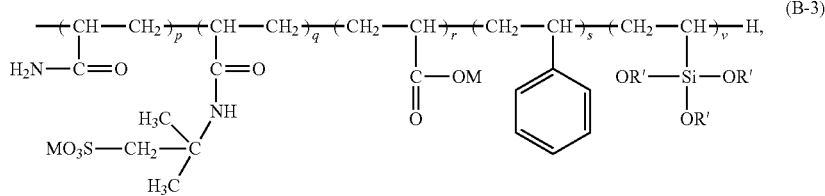
(B-3)

in these formulae, $R_9$ is ethylene, p is a number ranging from 0 to 30 or from 2 to 30, q is a number ranging from 0 to 30 or from 2 to 30, r is a number ranging from 0 to 30 or from 2 to 30, s is a number ranging from 2 to 30, and v is a number ranging from 0 to 30.

9. The aryl-substituted saccharide or glycoside or the mixture of a plurality of aryl-substituted saccharides or glycosides according to claim 7, which is one or more compounds selected from the group consisting of compounds represented schematically by the following formula (I-1), formula (I-2), formula (I-3) or formula (I-4),

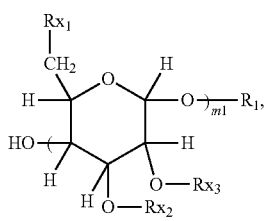
(I-1)

in formula (I-1), among $m_1$ number of $Rx_1$, one $Rx_1$ is said substituent A, while the remaining $Rx_1$, same as or different from each other, are each independently selected from said substituent A and hydroxyl group, wherein $m_1$ is an integer of 2 to 3, and $m_1$ number of $Rx_2$ and $m_1$ number of $Rx_3$, same as or different from each other, are each independently selected from the group consisting of a hydrogen atom and said substituent B, provided that at least one of these $Rx_2$ and $Rx_3$ is said substituent B,

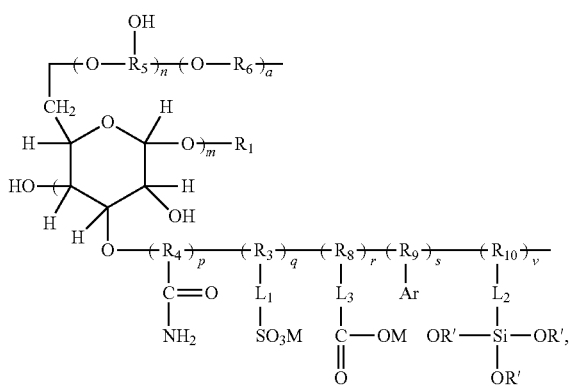
(I-2)

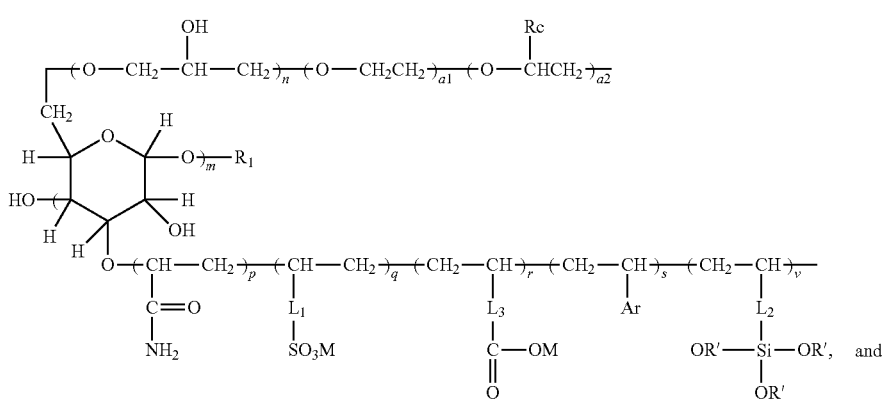
(I-3)

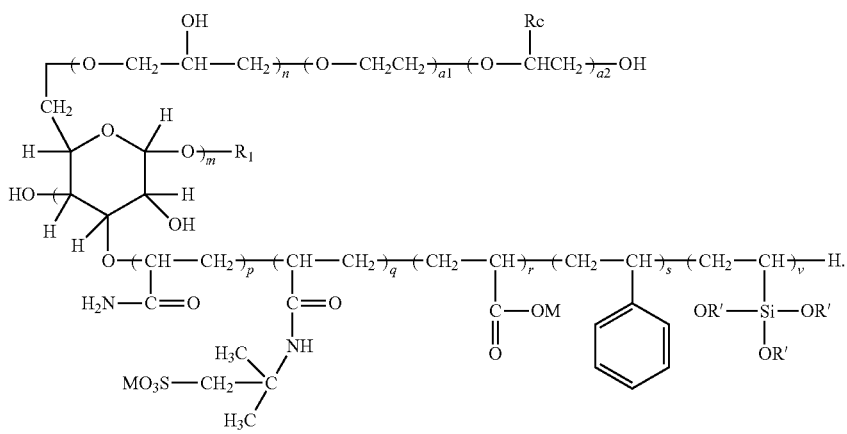
(I-4)

10. The aryl-substituted saccharide or glycoside or the mixture of a plurality of aryl-substituted saccharides or glycosides according to claim 8, wherein in formula (A-1), formula (A-2) or formula (A-3), n is 0, a is 8 to 12, a1 is a number ranging from 0 to 5, a2 is a number ranging from 8 to 12, and/or, in formula (B-1), formula (B-2) or formula (B-3), p is a number ranging from 10 to 20, q is a number ranging from 10 to 20, r is a number ranging from 10 to 20, s is a number ranging from 10 to 20, v is a number ranging from 4 to 12.

11. The aryl-substituted saccharide or glycoside or the mixture of a plurality of aryl-substituted saccharides or glycosides according to claim 3, wherein in formula (1), two occurrences of $R_1$, same as or different from one another, are each independently selected from octyl, decyl, dodecyl, tetradecyl, hexadecyl or octadecyl, and/or m is 2.

12. The aryl-substituted saccharide or glycoside or the mixture of a plurality of aryl-substituted saccharides or glycosides according to claim 4, having an amine value of from 0.20 to 0.50 mmol/g.

13. A drilling fluid composition comprising an aryl-substituted saccharide or glycoside and a base slurry, wherein the aryl-substituted saccharide or glycoside is an aryl-substituted saccharide or glycoside or a mixture of a plurality of aryl-substituted saccharides or glycosides according claim 1.

14. The drilling fluid composition according to claim 13, wherein the aryl-substituted saccharide or glycoside is present in an amount of 0.1 to 5wt% based on 100wt% of the total weight of the drilling fluid composition.

15. A process of producing an aryl-substituted saccharide or glycoside or a mixture of a plurality of aryl-substituted saccharides or glycosides comprising the steps of:

1) reacting a saccharide or glycoside represented schematically by the following formula (X-1) or formula (X-2), optionally in the presence of a catalyst, to obtain an etherified saccharide or glycoside,

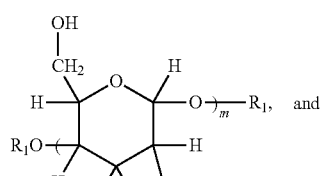
(X-1)

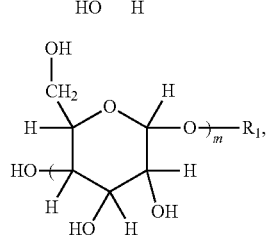
(X-2)

in formula (X-1) and formula (X-2), two $R_1$, same as or different from one another, are each independently selected from the group consisting of hydrogen and C1-20 linear or branched alkyl group, and m is an integer of 1 to 3, wherein the etherifying agent is an alkylene oxide monomer represented schematically by the following formula (A-11), a polyhydroxyl monomer represented schematically by the following formula (A-21) or a combination thereof,

(A-11)

in formula (A-11), Ra is a hydrogen atom or a C1-5 linear or branched alkyl group, and

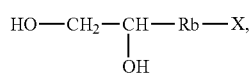
(A-21)

in formula (A-21), Rb is a C1-4 linear or branched alkylenyl group and X is a hydroxyl group or a halogen atom, 2) reacting the etherified saccharide or glycoside with an arylethylene monomer represented schematically by the following formula (B-11) or formula (B-12), optionally using an acrylamide monomer represented schematically by the following formula (B-21), optionally using a sulfoethylene monomer represented schematically by the following formula (B-31) or formula (B-32), optionally using a siloxyethylene monomer represented schematically by the following formula (B-41) or formula (B-42), and optionally using a carboxyethylene monomer represented schematically by the following formula (B-51) or formula (B-52) for the reaction, to obtain the aryl-substituted saccharide or glycoside or the mixture of a plurality of aryl-substituted saccharides or glycosides,

(B-11)

in formula (B-11), Ar is an optionally substituted C6-20 aryl group,

(B-12)

(B-21)

(B-31)

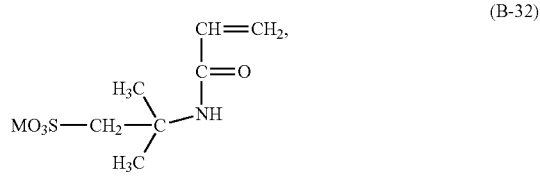
(B-32)

in formula (B-31) and formula (B-32), $L_1$ is any linking group having no more than 10 carbon atoms and M is hydrogen, alkali metal or ammonium ($NH_4$),

(B-41)

(B-42)

in formula (B-41) and formula (B-42), $L_2$ is any linking group having no more than 10 carbon atoms, and R' is a C1-4 linear or branched alkyl group,

(B-51)

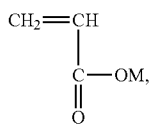

in formula (B-51) and formula (B-52), $L_3$ is any linking group having no more than 10 carbon atoms, and M is hydrogen, alkali metal, or ammonium ($NH_4$).

16. The process according to claim 15, wherein the reaction in step 1) is conducted at a temperature of 95 to 155° C. for 1 to 3 hours, and/or the reaction in step 2) is conducted at a temperature of 40 to 80° C. for 1 to 3 hours, and/or the weight ratio of the etherifying agent, the saccharide or glycoside and the catalyst is 24:(70-100):(10-30), and/or the weight ratio of the etherifying agent, the carboxyethylene monomer, the arylethylene monomer, the acrylamide monomer, the sulfoethylene monomer, the siloxyethylene monomer, and the initiator is 24:(20-40):(20-40):(20-40):(10-20):(10-20):(0.6-1.8).

17. A drilling fluid composition comprising an aryl-substituted saccharide or glycoside and a base slurry, wherein the aryl-substituted saccharide or glycoside is an aryl-substituted saccharide or glycoside or a mixture of a plurality of aryl-substituted saccharides or glycosides produced by the process of claim 15.

18. The process according to claim 15, wherein,
in step 1), the saccharide or glycoside is at least one selected from octyl glycoside, decyl glycoside, dodecyl glycoside, tetradecyl glycoside, hexadecyl glycoside or octadecyl glycoside, and/or,
the etherifying agent is at least one selected from the group consisting of propylene oxide, 1,2-butylene oxide and 1,2-pentylene oxide, and/or,
the catalyst is at least one selected from the group consisting of sodium carbonate, potassium carbonate, calcium oxide and magnesium oxide, and/or,
in formula (X-1) and formula (X-2), two $R_1$, same as or different from one another, are each independently selected from octyl, decyl, dodecyl, tetradecyl, hexadecyl or octadecyl, and/or
m is 2, and/or,
in formula (A-11), Ra is a hydrogen atom or a C1-3 linear or branched alkyl group, and/or,
in formula (A-21), Rb is a C1-2 linear or branched alkylenyl group, and/or
X is Cl or Br, and/or,
the reaction in step 2) is conducted by a radical polymerization in the presence of an initiator, and/or,
in formula (B-11), Ar is an optionally substituted phenyl group, and/or, in formula (B-31) and formula (B-32), $L_1$ is a single bond, C2-10 linear or branched alkylene, —C(=O)-C2-10 linear or branched alkylene, —C(=O)O-C2-10 linear or branched alkylene, —C(=O)NH-C2-10 linear or branched alkylene, C2-5 linear or branched alkylene-C(=O)C2-5 linear or branched alkylene, C2-5 linear or branched alkylene C(=O)O-C2-5 linear or branched alkylene, or C2-5 linear or branched alkylene C(=O)NH-C2-5 linear or branched alkylene, and/or,
in formula (B-41) and formula (B-42), $L_2$ is a single bond or C2-10 linear or branched alkylenyl group, and/or
R' is methyl or ethyl, and/or,
in formula (B-51) and formula (B-52), $L_3$ is a single bond or C2-10 linear or branched alkylenyl group.

19. The process according to claim 16, wherein the weight ratio of the etherifying agent, the saccharide or glycoside and the catalyst is 24: (75-95): (15-25), and/or, the weight ratio of the etherifying agent, the carboxyethylene monomer, the arylethylene monomer, the acrylamide monomer, the sulfoethylene monomer, the siloxyethylene monomer, and the initiator is 24: (25-35): (25-35): (25-35): (12-18): (12-18): (0.8-1.6).

* * * * *